(12) United States Patent
Leblanc et al.

(10) Patent No.: US 9,174,985 B2
(45) Date of Patent: Nov. 3, 2015

(54) SALTS OF 7-(2,3-DI-P-TOLYL-7,8-DIHYDROPYRIDO [2,3-B]PYRAZIN-5(6H)-YL)HEPTANOIC ACID AS IP RECEPTOR AGONISTS

(71) Applicants: Catherine Leblanc, Basel (CH); Stephen Carl McKeown, Hitchin (GB); Anett Perlberg, Gunzgen (CH); Nicola Tufilli, Moehlin (CH)

(72) Inventors: Catherine Leblanc, Basel (CH); Stephen Carl McKeown, Hitchin (GB); Anett Perlberg, Gunzgen (CH); Nicola Tufilli, Moehlin (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/371,593

(22) PCT Filed: Jan. 11, 2013

(86) PCT No.: PCT/IB2013/050283
§ 371 (c)(1),
(2) Date: Jul. 10, 2014

(87) PCT Pub. No.: WO2013/105066
PCT Pub. Date: Jul. 18, 2013

(65) Prior Publication Data
US 2015/0011555 A1  Jan. 8, 2015

Related U.S. Application Data

(60) Provisional application No. 61/586,324, filed on Jan. 13, 2012.

(51) Int. Cl.
C07D 471/04 (2006.01)

(52) U.S. Cl.
CPC .................................... *C07D 471/04* (2013.01)

(58) Field of Classification Search
CPC . A61K 31/4985; C07D 241/38; C07D 471/04
USPC ............................. 514/249; 544/350; 546/122
See application file for complete search history.

(56) References Cited

U.S. PATENT DOCUMENTS

| | | |
|---|---|---|
| 8,754,085 B2 | 6/2014 | Charlton et al. |
| 2010/0280041 A1 | 11/2010 | Chen et al. |
| 2013/0184282 A1 | 7/2013 | Adcock et al. |
| 2014/0357641 A1 | 12/2014 | Bhalay et al. |
| 2014/0357642 A1 | 12/2014 | Charlton et al. |
| 2014/0378463 A1 | 12/2014 | Leblanc |
| 2015/0005311 A1 | 1/2015 | Charlton et al. |

FOREIGN PATENT DOCUMENTS

| | | |
|---|---|---|
| WO | 2007/017096 A1 | 2/2007 |
| WO | 2010/008864 A1 | 1/2010 |
| WO | 2012/007539 A1 | 1/2012 |
| WO | 2013/105066 A1 | 7/2013 |
| WO | 2014/125413 A1 | 8/2014 |

*Primary Examiner* — Douglas M Willis
(74) *Attorney, Agent, or Firm* — Shawn Britt

(57) ABSTRACT

The invention relates to salts of (7-(2,3-di-p-tolyl-7,8-dihydropyrido[2,3-b]pyrazin-5(6H)-yl)heptanoic acid which are useful for treating diseases affected by the activation of the IP receptor, pharmaceutical compositions that contain the salts and processes for preparing the salts are also described.

9 Claims, 4 Drawing Sheets

SALTS OF 7-(2,3-DI-P-TOLYL-7,8-DIHYDROPYRIDO [2,3-B]PYRAZIN-5(6H)-YL)HEPTANOIC ACID AS IP RECEPTOR AGONISTS

CROSS REFERENCE TO RELATED APPLICATIONS

This application is a U.S. National Phase filing of International Application No. PCT/IB2013/050283 filed 11 Jan. 2013, which claims priority to U.S. Application No. 61/586,324 filed 13 Jan. 2012, the contents of which are incorporated herein by reference in their entirety.

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION BY REFERENCE OF MATERIAL SUBMITTED ON A COMPACT DISC

Not applicable

BACKGROUND OF THE INVENTION

This invention relates to novel salts of 7-(2,3-di-p-tolyl-7,8-dihydropyrido[2,3-b]pyrazin-5(6H)-yl)heptanoic acid, a process for their preparation and their use in pharmaceutical compositions.

International patent application PCT/EP2011/062028 (WO2012/007539) discloses certain heterocyclic compounds that are active IP receptor agonists and their use in treating various conditions or diseases affected by the activation of the IP receptor, including, for example, pulmonary arterial hypertension. One of those heterocyclic compounds is 7-(2,3-di-p-tolyl-7,8-dihydropyrido-[2,3-b]pyrazin-5(6H)-yl)heptanoic acid, which has the following structure:

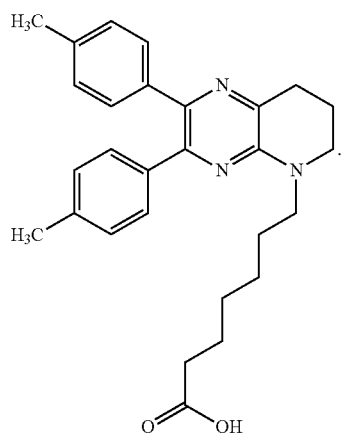 [SMILES: Cc1ccc(-c2nc3c(nc2-c2ccc(C)cc2)N(CCCCCCC(=O)O)CCC3)cc1]

International patent application PCT/EP2011/062028 (WO2012/007539) discloses a process for preparing 7-(2,3-di-p-tolyl-7,8-dihydropyrido[2,3-b]pyrazin-5(6H)-yl)heptanoic acid and the corresponding mesylate salt.

Pulmonary arterial hypertension (PAH) is a life-threatening disease characterized by a progressive pulmonary vasculopathy leading to right ventricular hypertrophy. Exogenous administration of an agonist of the IP receptor has become an important strategy in the treatment of PAH. (See, e.g., Tuder et al., *Am. J. Respir. Crit. Care. Med.*, 1999, 159: 1925-1932; Humbert et al, *J. Am. Coll. Cardiol.*, 2004, 43:13 S-24S; Rosenzweig, *Expert Opin. Emerging Drugs*, 2006, 11:609-619; McLaughlin et al, *Circulation*, 2006, 114:1417-1431; Rosenkranz, *Clin. Res. Cardiol.*, 2007, 96:527-541; Driscoll et al, *Expert Opin. Pharmacother.*, 2008, 9:65-81.).

A preferred route of administration of salts of 7-(2,3-di-p-tolyl-7,8-dihydropyrido[2,3-b]pyrazin-5(6H)-yl)heptanoic acid in the treatment of pulmonary arterial hypertension is pulmonary delivery by inhalation.

The free form of 7-(2,3-di-p-tolyl-7,8-dihydropyrido[2,3-b]pyrazin-5(6H)-yl)heptanoic acid has physical properties, including poor solubility and stability, that give rise to significant technical problems when manufacturing and formulating it for use as a pharmaceutical, particularly as an inhalable product, for example an inhalable dry powder.

The mesylate salt form of 7-(2,3-di-p-tolyl-7,8-dihydropyrido[2,3-b]pyrazin-5(6H)-yl)heptanoic acid is undesired mainly for toxicological reasons, not in respect of pure methanesulfonate (mesylate) salts, but rather for certain corresponding sulfonic acid esters that are known to exert genotoxic effects. Such esters can be formed during the synthesis of the drug substance or during the crystallization of the salt, or during storage, especially if the crystallization solvent contains alcohols, such as methanol, ethanol or propanol. They can also be formed when alcoholic solvents are used for the preparation of the dosage form.

It has now been found that at least some of issues can be overcome by preparing certain novel salts of 7-(2,3-di-p-tolyl-7,8-dihydropyrido[2,3-b]pyrazin-5(6H)-yl)heptanoic acid or at the very least such salts provide useful alternatives to the free form and the mesylate salt form.

SUMMARY OF THE INVENTION

In a first aspect, the present invention provides a compound selected from the group consisting of

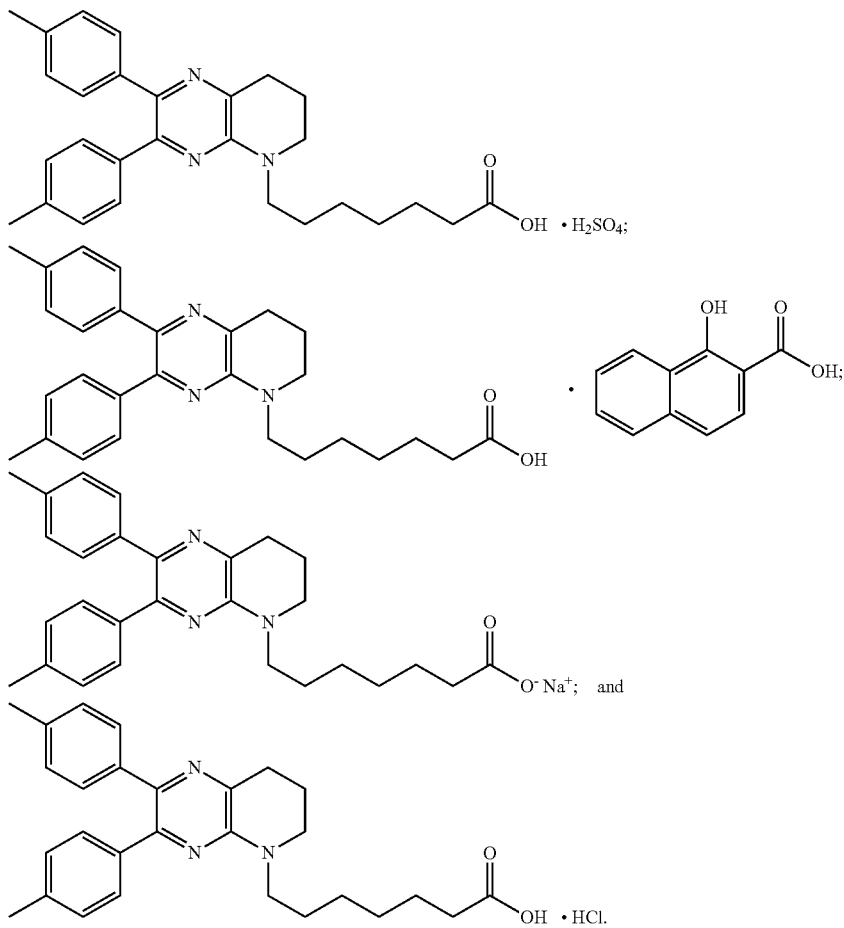

In an embodiment (i) of the first aspect, the compound is in crystalline form.

In an embodiment (ii) of the first aspect, the compound is

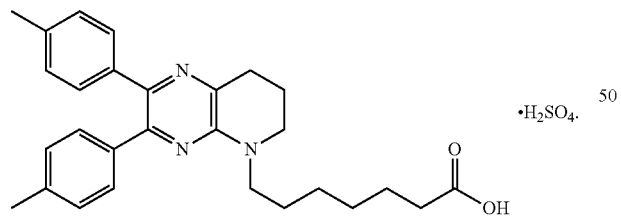

In an embodiment (iii) of the first aspect, the compound is

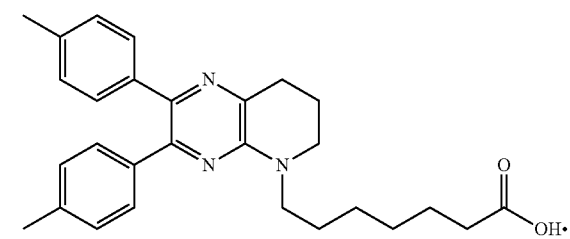

-continued

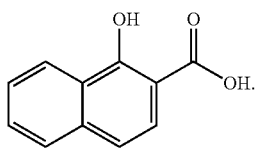

In an embodiment (iv) of the first aspect, the compound is

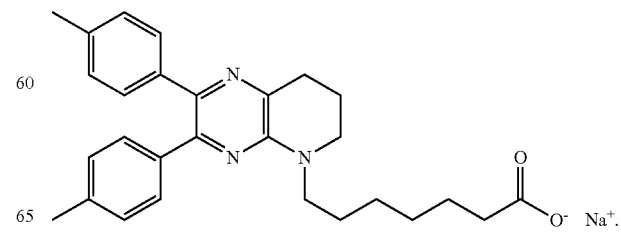

In an embodiment (v) of the first aspect, the compound is

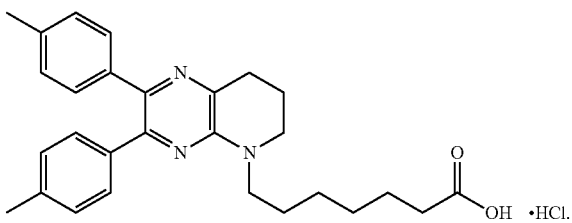

In an embodiment (vi) of the first aspect, the compound is of formula I

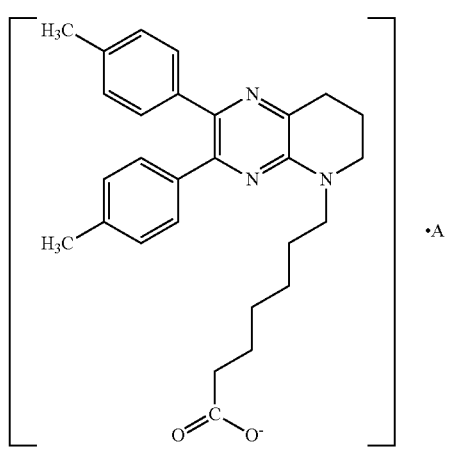

in salt or solvate form,
wherein A is selected from the group consisting of sulfate, xinafoate, sodium, hydrogen chloride, hydrogen bromide and L-arginine.

In an embodiment (vii) of the first aspect, the compound is
7-(2,3-di-p-tolyl-7,8-dihydropyrido[2,3-b]pyrazin-5(6H)-yl)heptanoate sulfate (sulfuric acid salt of 7-(2,3-di-p-tolyl-7,8-dihydropyrido[2,3-b]pyrazin-5(6H)-yl)heptanoic acid);
7-(2,3-di-p-tolyl-7,8-dihydropyrido[2,3-b]pyrazin-5(6H)-yl)heptanoate xinafoate (xinafoic acid salt of 7-(2,3-di-p-tolyl-7,8-dihydropyrido[2,3-b]pyrazin-5(6H)-yl)heptanoic acid),
7-(2,3-di-p-tolyl-7,8-dihydropyrido[2,3-b]pyrazin-5(6H)-yl)heptanoate sodium (sodium salt of
7-(2,3-di-p-tolyl-7,8-dihydropyrido[2,3-b]pyrazin-5(6H)-yl)heptanoic acid), and
7-(2,3-di-p-tolyl-7,8-dihydropyrido[2,3-b]pyrazin-5(6H)-yl)heptanoate hydrochloride (hydrogen chloride salt of 7-(2,3-di-p-tolyl-7,8-dihydropyrido[2,3-b]pyrazin-5(6H)-yl)heptanoic acid), especially crystalline forms thereof.

In a second aspect the invention provides a pharmaceutical composition comprising, as active ingredient, an effective amount of a compound as defined in the first aspect or embodiments (i)-(vii) of the first aspect, together with a pharmaceutically acceptable carrier.

In a preferred embodiment the composition is in inhalable form, for example an inhalable dry powder.

In a third aspect the invention provides a method of treating a condition or disease that is affected by the activation of the IP receptor comprising administering to a patient in need thereof an effective amount of a compound as defined in the first aspect or embodiments (i)-(vii) of the first aspect. In a preferred embodiment, the condition or disease affected by the activation of the IP receptor is selected from pulmonary arterial hypertension, atherosclerosis, asthma, COPD, hyperglycemia and fibrotic diseases. In certain preferred embodiments the condition or disease affected by the activation of the IP receptor is pulmonary arterial hypertension.

In a fourth aspect the invention concerns the use of a compound as defined in the first aspect or embodiments (i)-(vii) of the first aspect for the preparation of a medicament for the treatment of a condition or disease that is affected by the activation of the IP receptor. In a preferred embodiment, the condition or disease affected by the activation of the IP receptor is selected from pulmonary arterial hypertension, atherosclerosis, asthma, COPD, hyperglycemia and fibrotic diseases. In certain preferred embodiments the condition or disease affected by the activation of the IP receptor is pulmonary arterial hypertension.

In a fifth aspect, the present invention provides a compound as defined in the first aspect or embodiments (i)-(vii) of the first aspect for use in the treatment of a condition or disease that is affected by the activation of the IP receptor. In a preferred embodiment, the condition or disease affected by the activation of the IP receptor is selected from pulmonary arterial hypertension, atherosclerosis, asthma, COPD, hyperglycemia and fibrotic diseases. In certain preferred embodiments the condition or disease affected by the activation of the IP receptor is pulmonary arterial hypertension.

In a sixth aspect, the present invention provides an inhalation device that contains and is adapted to deliver a compound as defined in the first aspect or embodiments (i)-(vii) of the first aspect by pulmonary administration. In certain preferred embodiments the inhalation device is a dry powder inhaler, for example the BREEZHALER® inhalation device.

In a seventh aspect the invention provides a process for preparing a compound as defined in embodiments (vi) and (vii) of the first aspect that comprises:
(i) for the preparation of compounds as defined in the first aspect or embodiments (i)-(vii) of the first aspect where A is sulfate,
reacting the free form with sulfuric acid;
(ii) for the preparation of compounds as defined in the first aspect or embodiments (i)-(vii) of the first aspect where A is xinafoate,
reacting the free form with 1-hydroxy-2-naphthoic acid;
(iii) for the preparation of compounds as defined in the first aspect or embodiments (i)-(vii) of the first aspect where A is sodium,
reacting the free form with sodium hydroxide; or
(iv) for the preparation of compounds as defined in the first aspect or embodiments (i)-(vii) of the first aspect where A is hydrogen chloride,
reacting the free form with hydrochloric acid.

Terms used in the specification have the following meanings:

"Pulmonary arterial hypertension" or PAH as used herein is a life-threatening disease characterized by a progressive pulmonary vasculopathy leading to right ventricular hypertrophy. It includes idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH); Raynaud's phenomenon, including Raynaud's disease and Raynaud's syndrome; fibrotic diseases, including pulmonary fibrosis, systemic sclerosis/scleroderma, hepatic fibrosis/cirrhosis, renal fibrosis; thrombotic diseases associated with excessive platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, preeclampsia, inflammation, prophylaxis against unwanted side effects of COX-1, COX-2 and non-selective COX inhibitors, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

DETAILED DESCRIPTION OF THE INVENTION

Figure 1:
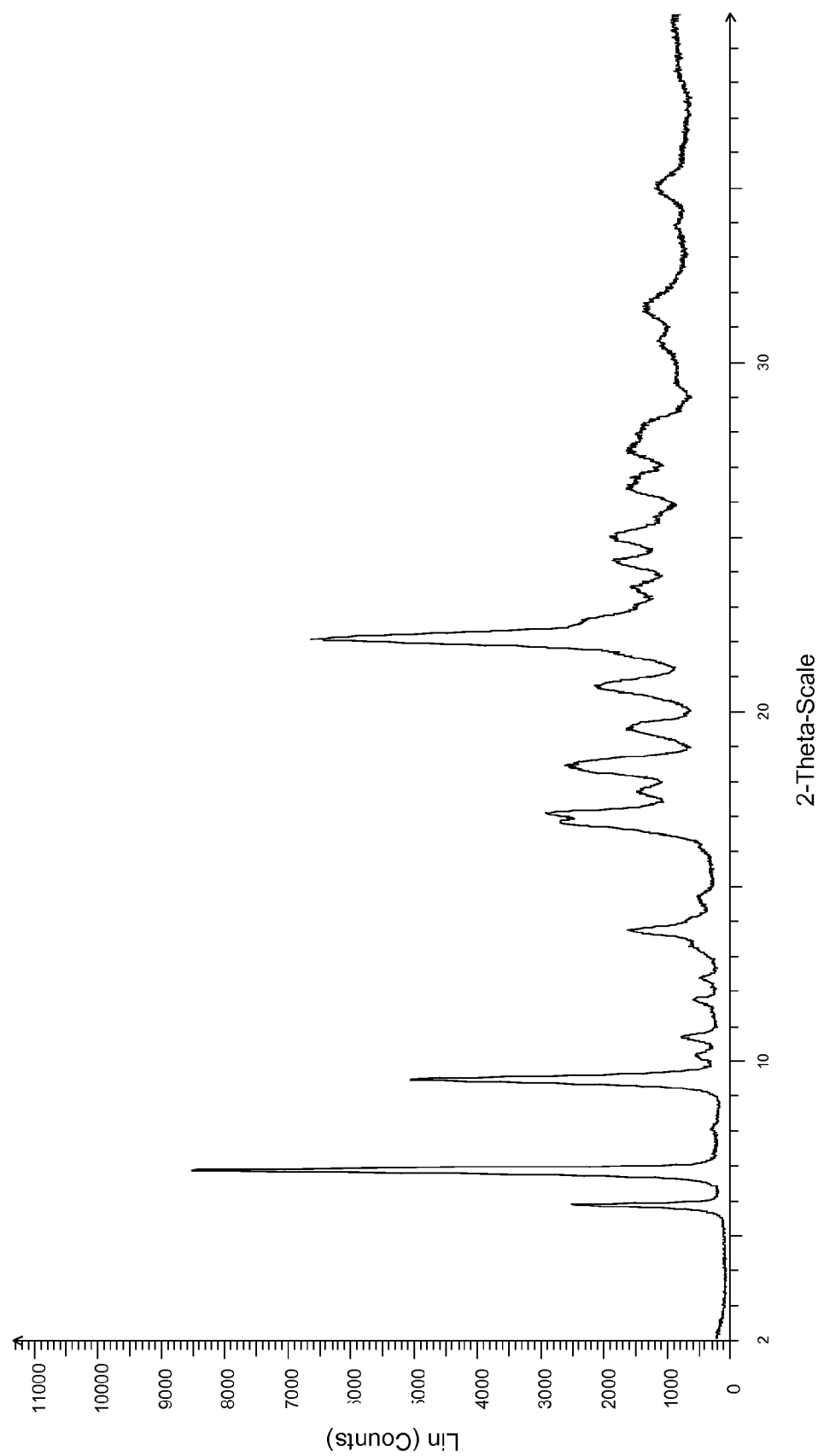
FIG. 1 is an x-ray powder diffraction pattern of the crystalline sulfuric acid salt of 7-(2,3-di-p-tolyl-7,8-dihydropyrido[2,3-b]pyrazin-5(6H)-yl)heptanoic acid.

The present invention provides certain salts of 7-(2,3-di-p-tolyl-7,8-dihydropyrido[2,3-b]pyrazin-5(6H)-yl)heptanoic acid, which is an active IP receptor agonist.

7-(2,3-di-p-tolyl-7,8-dihydropyrido[2,3-b]pyrazin-5(6H)-yl)heptanoic acid, i.e. the free form of compounds as defined in the first aspect or embodiments (i)-(vii) of the first aspect, is one of many heterocyclic compounds with IP receptor agonist activity that the Applicant described in international patent application PCT/EP2011/062028 (WO2012/007539).

International patent application PCT/EP2011/062028 (WO2012/007539), the contents of which is incorporated herein by reference, discloses a process for its preparing 7-(2,3-di-p-tolyl-7,8-dihydropyrido-[2,3-b]pyrazin-5(6H)-yl)heptanoic acid. However for completeness a method for preparing that compound is provided in the Examples section of the present patent specification.

A single crystalline form of 7-(2,3-di-p-tolyl-7,8-dihydropyrido[2,3-b]pyrazin-5(6H)-yl)heptanoic acid has been identified but it has been found to be poorly soluble in water and have low stability under light which brings significant technical challenges in formulating the compound, especially as an inhalable dry powder.

The mesylate salt of 7-(2,3-di-p-tolyl-7,8-dihydropyrido[2,3-b]pyrazin-5(6H)-yl)heptanoic acid, has tested favourably for the treatment of pulmonary arterial hypertension. However this salt, which is non-solvated, has been found to exhibit a significantly higher dissolution rate compared to the free form. A crystalline form of this salt has been found to entrap a significant amount of solvent in the crystal structure which is only released upon melting. Furthermore, and especially importantly, as mentioned above, certain sulfonic acid esters are known to exert genotoxic effects and great care must be taken to minimise and preferably prevent their synthesis during drug substance production and storage. Consequently the mesylate salt of 7-(2,3-di-p-tolyl-7,8-dihyrdropyrido[2,3-b]pyrazin-5(6H)-yl)heptanoic acid is difficult to formulate, especially as an inhalable dry powder.

The Applicant investigated a large number of alternative salts to address the aforementioned issues noted in formulating the compound. Only a small number of alternative salts were generated. Some of these salts were found to have physical properties that are amenable to drug substance development, for example in terms of the dissolution of drug substances, facilitated routes of manufacturing/purification and/or can be formulated as inhalable dry powders.

Surprisingly, the sulfuric acid salt of 7-(2,3-di-p-tolyl-7,8-dihydropyrido[2,3-b]pyrazin-5(6H)-yl)heptanoic acid has been found to exhibit good crystallinity and physical stability.

A crystalline form of this sulfuric acid salt has the following characteristic diffraction lines (2θ) in the X-ray diffraction pattern thereof with an intensity of 50% or higher: 6.8°, 9.4° and 22.1°. It has the following characteristic diffraction lines (2θ) in the same X-ray diffraction pattern thereof with an intensity of 25% or higher: 5.8°, 6.8°, 9.4°, 16.8°, 17.0°, 18.4°, 20.7°, 22.1° and 22.6°. The salt is also characterised by a melting point of 190° C.

Surprisingly, the xinafoic acid salt of 7-(2,3-di-p-tolyl-7,8-dihydropyrido[2,3-b]pyrazin-5(6H)-yl)heptanoic acid has been found to exhibit good crystallinity, physical stability and photostability.

A crystalline form of this xinafoic acid salt has the following characteristic diffraction lines (2θ) in the X-ray diffraction pattern thereof with an intensity of 50% or higher: 11.1°, 16.9°, 18.0°, 21.9°, 22.3° and 26.2°. It has the following characteristic diffraction lines (2θ) in the same X-ray diffraction pattern thereof with an intensity of 25% or higher: 6.5°, 9.8°, 11.1°, 16.4°, 16.9°, 18.0°, 18.3°, 19.2°, 19.5°, 19.8°, 20.1°, 20.7°, 21.0°, 21.9°, 22.3°, 23.8°, 24.9°, 26.2°, 26.6°, 27.7° and 31.5°. The salt is also characterised by a melting point of 153° C.

Surprisingly, the sodium salt of 7-(2,3-di-p-tolyl-7,8-dihydropyrido[2,3-b]pyrazin-5(6H)-yl)heptanoic acid has been found to exhibit good crystallinity and physical stability.

A crystalline form of this sodium salt has the following characteristic diffraction lines (2θ) in the X-ray diffraction pattern thereof with an intensity of 50% or higher: 9.3°, 18.6° and 22.1°. It has the following characteristic diffraction lines (2θ) in the same X-ray diffraction pattern thereof with an intensity of 25% or higher: 9.3°, 16.9°, 17.4°, 17.8°, 18.6°, 18.9°, 19.4°, 20.2°, 20.5°, 21.5°, 22.1°, 23.2°, 23.7°, 24.6° and 25.0°. The salt is also characterised by a melting point of 272° C.

Surprisingly, the hydrogen chloride salt of 7-(2,3-di-p-tolyl-7,8-dihydropyrido[2,3-b]pyrazin-5(6H)-yl)heptanoic acid has been found to exhibit good crystallinity and physical stability.

A crystalline form of this hydrogen chloride salt has the following characteristic diffraction lines (2θ) in the X-ray diffraction pattern thereof with an intensity of 50% or higher: 18.8°, 19.1°, 23.1° and 23.5°. It has the following characteristic diffraction lines (2θ) in the same X-ray diffraction pattern thereof with an intensity of 25% or higher: 7.7°, 18.8°, 19.1°, 19.8°, 23.1°, 23.5°, 25.7°, 26.6° and 30.6°. The salt is also characterised by a melting point of 153° C.

Certain compounds as defined in the first aspect or embodiments (i)-(vii) of the first aspect are prepared by reacting the free form (or free base) with the relevant acid, or analogously as described in the Examples using processes known in the art for forming acid addition salts from secondary amines. For example, for embodiments (ii), (iii) and (v) of the first aspect, the relevant acid is sulfuric acid, 1-hydroxy-2-naphthoic acid (xinafoic acid) and hydrochloric acid, respectively.

7-(2,3-di-p-tolyl-7,8-dihydropyrido[2,3-b]pyrazin-5(6H)-yl)heptanoic acid exhibits an acidic and a basic function in the same molecule. It acts as an acid when reacting with sodium hydroxide, i.e. the acidic group of the free form of the compound is responsible for salt formation. Accordingly the sodium salt of the 7-(2,3-di-p-tolyl-7,8-dihydropyrido[2,3-b]pyrazin-5(6H)-yl)heptanoic acid is prepared by reacting 7-(2,3-di-p-tolyl-7,8-dihydropyrido[2,3-b]pyrazin-5(6H)-yl)heptanoic acid with sodium hydroxide.

Formulation and Administration

The present invention also provides a pharmaceutical composition comprising, as active ingredient, an effective amount of a compound as defined in the first aspect or embodiments (i)-(vii) of the first aspect, together with a pharmaceutically acceptable carrier.

The agents of the invention may be administered by any appropriate route, e.g., orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound as defined in the first aspect or embodiments (i)-(vii) of the first aspect, optionally together with a pharmaceutically acceptable diluent or carrier therefor. The composition may contain a co-therapeutic agent, such as an anti-inflammatory, bronchodilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

In certain preferred embodiments the pharmaceutical composition of the present invention is in inhalable form.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., a compound as defined in the first aspect or embodiments (i)-(vii) of the first aspect having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula I either dissolved, or suspended, in a vehicle containing water, a co-solvent, such as ethanol or propylene glycol and a stabilizer, which may be a surfactant.

Further aspects of the invention include:

(a) a compound as defined in the first aspect or embodiments (i)-(vii) of the first aspect in inhalable form, e.g., in an aerosol or other atomisable composition or in inhalable particulate, e.g., micronised form;

(b) an inhalable medicament comprising a compound as defined in the first aspect or embodiments (i)-(vii) of the first aspect in inhalable form;

(c) a pharmaceutical product comprising a compounds as defined in the first aspect or embodiments (i)-(vii) of the first aspect in inhalable form in association with an inhalation device; and (d) an inhalation device containing a compound as defined in the first aspect or embodiments (i)-(vii) of the first aspect in inhalable form.

Dosages of compounds as defined in the first aspect or embodiments (i)-(vii) of the first aspect employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Suitable devices for delivery of dry powder in encapsulated form include those described in international patent application WO 05/113042 (including the BREEZHALER™ device) and U.S. Pat. No. 3,991,761 (including the AEROLIZER™ device). Suitable MDDPI devices include those described in WO 97/20589 (including the CERTIHALER™ device), WO 97/30743 (including the TWISTHALER™ device) and WO 05/37353 (including the GYROHALER™ device).

Dosages of agents of the invention employed in practising the present invention will of course vary depending, for example, on the particular condition to be treated, the effect desired and the mode of administration. In general, suitable daily dosages for administration by inhalation are of the order of 0.005 to 10 mg, while for oral administration suitable daily doses are of the order of 0.05 to 100 mg.

Pharmaceutical Use and Assay

Compounds as defined in the first aspect or embodiments (i)-(vii) of the first aspect are useful as pharmaceuticals. In particular, the compounds are suitable as IP receptor agonists and may be tested in the following assays.

Activity of compounds at the IP receptor (IP receptor) is assessed by measuring cAMP accumulation in CHO cells stably expressing the IP receptor (CHO-IP) using the PerkinElmer AlphaScreen assay. This technology measures the endogenous production of cAMP, in a non-radioactive luminescence proximity homogenous assay. A biological reaction occurs between streptavidin coated donor beads, biotinylated cAMP and anti-cAMP acceptor beads, bringing the donor and acceptor beads close enough together so that upon excitation a fluorescence signal is produced. On production of endogenous cAMP, competition between the biotinylated cAMP and cellular-derived cAMP causes a reduction in the fluorescent signal. The reduction in signal is proportional to the amount of cAMP being produced, thus it is possible to quantify the amount of cAMP being produced on stimulation with agonist.

Test and reference compounds are prepared at 100×[final] in 100% DMSO, and diluted 1:3 using a Biomek Fx (Beckman Coulter). This is followed by an intermediate dilution to give 5×[final] in assay buffer (HBSS containing 5 mM HEPES, 0.1% (w/v) BSA). 5 µL of 5×[final] test compounds, reference compounds and buffer/DMSO control are then transferred to a 384-well white OptiPlate, containing 20 µL CHO-IP cell suspension (15,000 cells/well, prepared from frozen), and plate is incubated at room temperature for 1 hour. A cAMP standard curve is constructed for each experiment (concentration range of 10000 nM to 0.001 nM, in assay buffer) and 25 µL of each concentration added to the last two columns of the assay plate. The incubation is terminated by the addition of lysis buffer (dH$_2$O; 0.3% (v v$^{-1}$) Tween-20) containing 20 units mL$^{-1}$ streptavidin coated donor beads and biotinylated cAMP (pre-incubated for 30 minutes) and 20 units mL$^{-1}$ anti-cAMP acceptor beads, which are added to the lysis buffer just before addition to the assay plate. The assay plate is then incubated at room temperature in the dark, for 60 minutes with gentle shaking, and read on the Envision plate reader (Perkin Elmer).

The raw data of the reference compounds, test compounds and controls are converted into cAMP concentrations, using the cAMP standard curve, in GraphPadPrism (GraphPad Software Inc). EC$_{50}$ as well as maximal values of the agonist curves are determined using a 4-parameter logistic equation. The % maximum response values of all test compounds are determined using the top of the treprostinil concentration-response curve.

7-(2,3-di-p-tolyl-7,8-dihydropyrido[2,3-b]pyrazin-5(6H)-yl)heptanoic acid has an EC$_{50}$ value in the data measurements described above of 0.00011 µM.

Therapeutic Use

The present invention also provides a method of treating a condition or disease that is affected by the activation of the IP receptor comprising administering to a patient in need thereof an effective amount of a compound as defined in the first aspect or embodiments (i)-(vii) of the first aspect.

The present invention also concerns the use of a compound as defined in the first aspect or embodiments (i)-(vii) of the first aspect for the preparation of a medicament for the treatment of a condition or disease that is affected by the activation of the IP receptor.

The present invention also provides compounds as defined in the first aspect or embodiments (i)-(vii) of the first aspect in salt or solvate form for use in the treatment of a condition or disease that is affected by the activation of the IP receptor.

The compounds as defined in the first aspect or embodiments (i)-(vii) of the first aspect, hereinafter referred to alternatively as "agents of the invention" activate the IP receptor and are useful in the treatment of several diseases and disorders, and in the amelioration of symptoms thereof.

Without limitation, conditions or diseases that are affected by the activation of the IP receptor include pulmonary arterial hypertension (PAH), conditions related to platelet aggregation, atherosclerosis, asthma, chronic obstructive pulmonary disease (COPD), hyperglycemia, inflammatory conditions and fibrosis. In certain preferred embodiments the condition or disease affected by the activation of the IP receptor is pulmonary arterial hypertension.

Pulmonary Arterial Hypertension

Pulmonary arterial hypertension (PAH) has a multifactorial pathobiology. Vasoconstriction, remodeling of the pulmonary vessel wall, and thrombosis contribute to increased pulmonary vascular resistance in PAH (Humbert et al, J. Am. Coll. Cardiol., 2004, 43:13 S-24S.). The compounds of the present invention disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (BPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HTV infection, PAH associated with drugs or toxins, or PAH associated with Other; and PAH associated with significant venous or capillary involvement. Idiopathic PAH refers to PAH of undetermined cause. Familial PAH refers to PAH for which hereditary transmission is suspected or documented. PAH associated with collagen vascular disease shall be understood to encompass PAH associated with scleroderma, PAH associated with CREST (calcinosis cutis, Raynaud's phenomenon, esophageal dysfunction, sclerodactyl), and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis. PAH associated with congenital systerruc-to-pulmonary shunts shall be understood to encompass PAH associated with atrial septic defect (ASD), PAH associated with ventricular septic defect (VSD) and PAH associated with patent ductus arteriosus.

PAH associated with drugs or toxins shall be understood to encompass PAH associated with ingestion of a minorex, PAH associated with ingestion of a fenfluramine compound (e.g., PAH associated with ingestion of fenfluramine or PAH associated with ingestion of dexfenfluramine), PAH associated with ingestion of certain toxic oils (e g, PAH associated with ingestion of rapeseed oil), PAH associated with ingestion of pyrrolizidine alkaloids (e.g., PAH associated with ingestion of bush tea) and PAH associated with ingestion of monocrotaline. PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy. PAH associated with significant venous or capillary involvement shall be understood to encompass PAH associated with pulmonary veno-occlusive disease (PVOD) and PAH associated with pulmonary capillary hemangiomatosis (PCH). (See, e.g., Simonneau et al., J. Am. Coll. Cardiol., 2004, 43:5 S-12S; McGoon et al., Chest, 2004, 126:14 S-34S; Rabinovitch, Annu. Rev. Pathol. Mech. Dis., 2007, 2:369-399; McLaughlin et al., Circulation, 2006, 114:1417-1431; Strauss et al., Clin. Chest. Med., 2007, 28:127-142; Taichman et al., Clin. Chest. Med., 2007, 28:1-22.).

Evidence for the association of PAH with scleroderma and the beneficial effect of an agonist of the IP receptor on PAH is given by Badesch et al. (Badesch et al., Ann. Intern. Med., 2000, 132:425-434). Evidence for the association of PAH with the collagen vascular diseases mixed connective tissue disease (MCTD), systemic lupus erythematosus (SLE), Sjogren's syndrome and CREST syndrome and the beneficial effect of an agonist of the IP receptor on PAH is given by Humbert et al. (Eur. Respir. J., 1999, 13:1351-1356). Evidence for the association of PAH with CREST syndrome and the beneficial effect of an agonist of the IP receptor on PAH is given by Miwa et al. (Int. Heart J., 2007, 48:417-422). Evidence for the association of PAH with SLE and the beneficial effect of an agonist of the IP receptor on PAH is given by Robbins et al. (Chest, 2000, 117:14-18). Evidence for the association of PAH with HIV infection and the beneficial of an agonist of the IP receptor on PAH is given by Aguilar et al. (Am. J. Respir. Crit. Care Med., 2000, 162:1846-1850). Evidence for the association of PAH with congenital heart defects (including ASD, VSD and patent ductus arteriosus) and the beneficial effect of an agonist of the IP receptor on PAH is given by Rosenzweig et al. (Circulation, 1999, 99:1858-1865).

Evidence for the association of PAH with fenfluramine and with dexfenfluramine, anorexigens, is given by Archer et al. (Am. J. Respir. Crit. Care Med., 1998, 158: 1061-1067). Evidence for the association of PAH with hereditary hemorrhagic telangiectasia is given by McGoon et al. (Chest, 2004, 126:14-34). Evidence for the association of PAH with splenectomy is given by Hoeper et al. (Ann. Intern. Med., 1999, 130:506-509). Evidence for the association of PAH with portal hypertension and the beneficial effect of an agonist of the IP receptor on PAH is given by Hoeper et al. (Eur. Respir. J., 2005, 25:502-508).

Symptoms of PAH include dyspnea, angina, syncope and edema (McLaughlin et al., Circulation, 2006, 114:1417-1431). The compounds of the present invention disclosed herein are useful in the treatment of symptoms of PAH.

Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction, the heart muscle does not receive enough oxygen-rich blood as a result of a blockage in the coronary blood vessels. If taken while an attack is in progress or immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs. Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes. Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that an IP receptor agonist will inhibit platelet aggregation and thus be a potential treatment as an antiplatelet therapy (see, e.g., Moncada et al., Lancet, 1977, 1:18-20). It has been shown that genetic deficiency of the IP receptor in mice leads to an increased propensity towards thrombosis (Murata et al, Nature, 1997, 388:678-682).

IP receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g., Fetalvero et al, Prostaglandins Other Lipid Mediat., 2007, 82:109-118; Arehart et al, Curr. Med. Chem., 2007, 14:2161-2169; Davi et al, N. Engl. J. Med., 2007, 357:2482-2494; Fetalvero et al, Am. J. Physiol. Heart. Circ. Physiol., 2006, 290:H1337-H1346; Murata et al, Nature, 1997, 388:678-682; Wang et al, Proc. Natl. Acad. Sci. USA, 2006, 103:14507-14512; Xiao et al, Circulation, 2001, 104:2210-2215; McCormick et al, Biochem. Soc. Trans., 2007, 35:910-911; Arehart et al, Circ. Res., 2008 Mar. 6.).

IP receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. IP receptor agonists can also be used in antiplatelet therapies in combination with, for example, alpha-tocopherol (vitamin E), echistatin (a disintegrin) or, in states of hypercoagulability, heparin. (See, e.g., Chan., J. Nutr., 1998, 128: 1593-1596; Mardla et al, Platelets, 2004, 15:319-324; Bernabei et al, Ann. Thorac. Surg., 1995, 59:149-153; Gainza et al, J. Nephrol., 2006, 19:648-655.)

The IP receptor agonists disclosed herein provide beneficial improvement in microcirculation to patients in need of antiplatelet therapy by antagonizing the vasoconstrictive products of the aggregating platelets in, for example and not limited to the indications described above.

Accordingly, in some embodiments, the present invention provides methods for reducing platelet aggregation in a patient in need thereof, comprising administering to the patient a composition comprising an IP receptor agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising an IP receptor agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising an IP receptor agonist disclosed herein at a time where such risk exists.

Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the IP receptor can confer protection from atherosclerosis, such as from atherothrombosis (Arehart et al., *Curr. Med. Chem.*, 2007, 14:2161-2169; Stitham et al., *Prostaglandins Other Lipid Mediat.*, 2007, 82:95-108; Fries et al., *Hematology Am. Soc. Hematol. Educ. Program,* 2005, 445-451; Egan et al., *Science,* 2004, 306:1954-1957; Kobayashi et al., *J. Clin. Invest,* 2004, 114: 784-794; Arehart et al., *Circ. Res.,* 2008 Mar. 6). It has been shown that defective IP receptor signaling appears to accelerate atherothrombosis in humans, i e that an agonist of the IP receptor can confer protection from atherothrombosis in humans (Arehart et al., *Circ. Res.,* 2008 Mar. 6.)

The compounds of the present invention disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a composition comprising an IP receptor agonist disclosed herein. In further embodiments, methods are provided for treating a symptom of atherosclerosis in a patient in need of the treatment, comprising administering to the patient a composition comprising an IP receptor agonist disclosed herein.

Asthma

Asthma is a lymphocyte-mediated inflammatory airway disorder characterised by airway eosinophilia, increased mucus production by goblet cells, and structural remodeling of the airway wall. The prevalence of asthma has dramatically increased worldwide in recent decades. It has been shown that genetic deficiency of the IP receptor in mice augments allergic airway inflammation (Takahashi et al., *Br. J. Pharmacol,* 2002, 137:315-322). It has been shown that an agonist of the IP receptor can suppress not only the development of asthma when given during the sensitization phase, but also the cardinal features of experimental asthma when given during the challenge phase (Idzko et al., *J. Clin. Invest.,* 2007, 117:464-72, Nagao et al., *Am. J. Respir. Cell Mol. Biol.,* 2003, 29:314-320), at least in part through markedly interfering with the function of antigen-presenting dendnuc cells within the airways (Idzko et al., *J. Clin. Invest.,* 2007, 117:464-472; Zhou et al., *J. Immunol.,* 2007, 178:702-710; Jaffar et al., *J. Immunol.,* 2007, 179:6193-6203; Jozefowski et al., *Int. Immunopharmacol.,* 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al., *J. Exp. Med.,* 2005, 201:981-991). It has also been shown that an agonist of the IP receptor can inhibit proinflammatory cytokine secretion by human alveolar macrophages (Raychaudhuri et al., *J. Biol. Chem.,* 2002, 277:33344-33348). The compounds of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising a IP receptor agonist disclosed herein.

In further embodiments, methods are provided for treating a symptom of asthma in a patient in need of the treatment, comprising administering to the patient a composition comprising a IP receptor agonist disclosed herein.

Chronic Obstructive Pulmonary Disease

Activation of the IP-receptor may also be beneficial in chronic obstructive pulmonary disease (COPD). Taprostene, an IP-receptor agonist, suppressed the generation of the CD8+ T cell chemoattractants CXCL9 and CXCL10 from human airway epithelial cells in vitro (Ayer, L. M., S. M. Wilson, S. L. Traves, D. Proud, M. A. Giembycz. 2008. *J. Pharmacol. Exp. Ther.* 324: 815-826.). Beraprost, an IP-receptor agonist, protected rats against the development of experimental cigarette smoke-induced emphysema, possibly by means of a concerted inhibitory action on alveolar epithelial cell apoptosis, oxidative burden, matrix metalloproteinase expression, and proinflammatory cytokine generation. (Chen, Y., M. Hanaoka, P. Chen, Y. Droma, N. F. Voelkel, K. Kubo. 2009. *Am. J. Physiol.* 296: L648-L656.)

In further embodiments, methods are provided for treating COPD in a patient in need of the treatment, comprising administering to the patient a composition comprising IP receptor agonist disclosed herein.

Hyperglycemia

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron et al., *Naunyn Schmiedebergs Arch. Pharmacol.,* 2003, 367:607-614). Agonists of the IP receptor promote vasodilation and inhibit platelet aggregation. Improving microvascular blood flow is able to benefit diabetic complications (Cameron, *Diabetologia,* 2001, 44:1973-1988).

It has been shown that an agonist of the IP receptor can prevent and reverse motor and sensory peripheral nerve conduction abnormalities in streptozotocin-diabetic rats (Cotter et al., *Naunyn Schmiedebergs Arch. Pharmacol.,* 1993, 347: 534-540). Further evidence for the beneficial effect of an agonist of the IP receptor in the treatment of diabetic peripheral neuropathy is given by Hotta et al. (*Diabetes,* 1996, 45:361-366), Ueno et al. (*Jpn. J. Pharmacol.,* 1996, 70:177-182), Ueno et al. (*Life Sci.,* 1996, 59:PL105-PL110), Hotta et al. (*Prostaglandins,* 1995, 49:339-349), Shindo et al. (*Prostaglandins,* 1991, 41:85-96), Okuda et al. (*Prostaglandins,* 1996, 52:375-384), and Koike et al. (*FASEB J.,* 2003, 17:779-781).

Evidence for the beneficial effect of an agonist of the IP receptor in the treatment of diabetic nephropathy is given by Owada et al. (*Nephron,* 2002, 92:788-796) and Yamashita et al. (*Diabetes Res. Clin. Pract.,* 2002, 57:149-161). Evidence for the beneficial effect of an agonist of the IP receptor in the treatment of diabetic retinopathy is given by Yamagishi et al. (*Mol. Med.,* 2002, 8:546-550), Burnette et al. (*Exp. Eye Res.,* 2006, 83: 1359-1365), and Hotta et al. (*Diabetes,* 1996, 45:361-366). It has been shown that an agonist of the IP receptor can reduce increased tumor necrosis factor-[alpha] (TNF-[alpha]) levels in diabetic patients, implying that an agonist of the IP receptor may contribute to the prevention of progression in diabetic complications (Fujiwara et al, *Exp. Clin. Endocrinol. Diabetes,* 2004, 112:390-394).

Evidence that topical administration of an agonist of the IP receptor can result in a decrease in intraocular pressure (IOP) in rabbits and dogs and thereby have beneficial effect in the treatment of glaucoma is given by Hoyng et al. (Hoyng et al, *Invest. Ophthalmol. Vis. Sci.,* 1987, 28:470-476).

Agonists of the IP receptor have been shown to have activity for regulation of vascular tone, for vasodilation, and for amelioration of pulmonary hypertension (see, e.g., Strauss et al, *Clin Chest Med,* 2007, 28:127-142; Driscoll et al, *Expert Opin. Pharmacother.,* 2008, 9:65-81). Evidence for a beneficial effect of an agonist of the IP receptor in the treatment of hypertension is given by Yamada et al. (*Peptides,* 2008, 29:412-418). Evidence that an agonist of the IP receptor can protect against cerebral ischemia is given by Dogan et al.

(*Gen. Pharmacol.*, 1996, 27:1163-1166) and Fang et al. (*J. Cereb. Blood Flow Metab.*, 2006, 26:491-501).

Anti-Inflammation

Anti-inflammation agents are prescribed for a variety of conditions. For example, in an inflammatory disease they are used to interfere with and thereby reduce an underlying deleterious.

There is evidence that an IP receptor agonist can inhibit inflammation and thus be a potential treatment as an anti-inflammation therapy. It has been shown that an agonist of the IP receptor can inhibit pro-inflammatory cytokine and chemokine (interleukin-12 (IL-12), tumor necrosis factor-[alpha] (TNF-[alpha]), DL-I[alpha], EL-6, macrophage inflammatory protein-1 alpha (MIP-I[alpha]), monocyte chemoattractant protein-1 (MCP-I)) production and T cell stimulatory function of dendritic cells (Jozefowski et al, *Int. Immunopharmacol.*, 2003, 865-878; Zhou et al, *J. Immunol.*, 2007, 178:702-710; Nagao et al, *Am. J. Respir. Cell Mol. Biol.*, 2003, 29:314-320; Idzko et al., *J. Clin. Invest.*, 2007, 117:464-472). It has been shown that an agonist of the IP receptor can inhibit pro-inflammatory cytokine (TNF-[alpha], IL-1/3, EL-6, granulocyte macrophage stimulating factor (GM-CSF)) production by macrophages (Raychaudhuri et al, *J. Biol. Chem.*, 2002, 277:33344-33348; Czeslick et al, *Eur. J. Clin. Invest.*, 2003, 33:1013-1017; Di Renzo et al, *Prostaglandin Leukot. Essent. Fatty Acids*, 2005, 73:405-410; Shinomiya et al, *Biochem. Pharmacol.*, 2001, 61:1153-1160). It has been shown that an agonist of the IP receptor can stimulate anti-inflammatory cytokine (DL-10) production by dendritic cells (Jozefowski et al, *Int. Immunopharmacol.*, 2003, 865-878; Zhou et al, *J. Immunol.*, 2007, 178:702-710). It has been shown that an agonist of the IP receptor can stimulate anti-inflammatory cytokine (DL-10) production by macrophages (Shinomiya et al., *Biochem. Pharmacol.*, 2001, 61: 1153-1160). It has been shown that an agonist of the IP receptor can inhibit a chemokine (CCL 17)-induced chemotaxis of leukocytes (CD4<+>Th2 T cells) (Jaffar et al, *J. Immunol.*, 2007, 179:6193-6203). It has been shown that an agonist of the IP receptor can confer protection from atherosclerosis, such as from atherothrombosis (Arehart et al, *Curr. Med. Chem.*, 2007, 14:2161-2169; Stitham et al, *Prostaglandins Other Lipid Mediat.*, 2007, 82:95-108; Fries et al, *Hematology Am. Soc. Hematol. Educ. Program*, 2005, 445-451; Egan et al, *Science*, 2004, 306:1954-1957; Kobayashi et al, *J. Clin. Invest.*, 2004, 114:784-794; Arehart et al, *Circ. Res.*, 2008 Mar. 6). It has been shown that an agonist of the IP receptor can attenuate asthma (Idzko et al, *J. Clin. Invest.*, 2007, 117:464-472; Jaffar et al, *J. Immunol.*, 2007, 179:6193-6203; Nagao et al, *Am. J. Respir. Cell. Mol. Biol.*, 2003, 29:314-320). It has been shown that an agonist of the IP receptor can decrease TNF-[alpha] production in type 2 diabetes patients (Fujiwara et al, *Exp. Clin. Endocrinol. Diabetes*, 2004, 112:390-394; Goya et al, *Metabolism*, 2003, 52: 192-198). It has been shown that an agonist of the IP receptor can inhibit ischemia-reperfusion injury (Xiao et al, *Circulation*, 2001, 104:2210-2215). It has been shown that an agonist of the IP receptor can inhibit restenosis (Cheng et al, *Science*, 2002, 296:539-541). It has been shown that an agonist of the IP receptor can attenuate pulmonary vascular injury and shock in a rat model of septic shock (Harada et al, *Shock*, 2008 Feb. 21). It has been shown that an agonist of the IP receptor can reduce the serum levels of TNF-[alpha] in vivo in patients with rheumatoid arthritis, and this is associated with improvement in the clinical course of the disease (Gao et al, *Rheumatol. Int.*, 2002, 22:45-51; Boehme et al, *Rheumatol. Int.*, 2006, 26:340-347).

The compounds of the present invention disclosed herein provide beneficial reduction of inflammation. The compounds of the present invention disclosed herein provide beneficial reduction of a deleterious inflammatory response associated with an inflammatory disease. Accordingly, in some embodiments, the present invention provides methods for reducing inflammation in a patient in need thereof, comprising administering to the patient a composition comprising an IP receptor agonist disclosed herein. In some embodiments, the present invention provides methods for decreasing IL-12, TNF-[alpha], IL-I[alpha], IL-IjS, BL-6, MIP-Ia or MCP-I production in a patient in need thereof, comprising administering to the patient a composition comprising an IP receptor agonist disclosed herein. In some embodiments, the present invention provides methods for decreasing TNF-[alpha] production in a patient in need thereof, comprising administering to the patient a composition comprising an IP receptor agonist disclosed herein. In some embodiments, the present invention provides methods for increasing EL-IO production in a patient in need thereof, comprising administering to the patient a composition comprising an IP receptor agonist disclosed herein. In some embodiments, the present invention provides methods for reducing a deleterious inflammatory response associated with an inflammatory disease in a patient in need thereof, comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein. In some embodiments, the present invention provides methods for treating an inflammatory disease or a symptom thereof in a patient in need of the treatment comprising administering to the patient a composition comprising an IP receptor agonist disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

Fibrosis

PGI2 signaling has been shown to play a beneficial role in fibrotic diseases of various organs, including kidney, heart, lung, skin, pancreas and liver, as well as in systemic sclerosis and associated pathologies. It has been shown that an agonist of the IP receptor can ameliorate cardiac fibrosis (Chan E C et al. (2010) *J Mol Cell Cardiol*. April 18; Hirata Y et al. (2009) *Biomed Pharmacother.* 63(10):781-6; Kaneshige T et al. (2007) *J Vet Med. Sci.* 69(12):1271-6). It has been shown that an agonist of the IP receptor can attenuate renal fibrosis (Takenaka M et al. (2009) *Prostaglandins Leukot Essent Fatty Acids.* 80(5-6):263-7). It has been shown that an agonist of the IP receptor can protect against pulmonary fibrosis in a bleomycin model (Zhu Y et al. (2010) *Respir Res.* 20; 11(1):34). It has been shown that an agonist of the IP receptor can suppress the production of connective tissue growth factor, a key mediator of fibrosis, in scleroderma patients (Stratton R et al. (2001) *J Clin Invest.* 108(2):241-50). It has been shown that an agonist of the IP receptor can reduce the incidence of digital ulcerations in patients with systemic sclerosis M. Vayssairat (1999) *J Rheumatol* 26:2173-2178. It has been shown that an agonist of the IP receptor can reduce fingertip necrosis in infants with refractory Renaud's phenomenon (Shouval D S et al. (2008) *Clin Exp Rheumatol.* 26(3 Suppl 49):S105-7). It has been shown that an agonist of the IP receptor can reduce markers of endothelial activation in patients with systemic sclerosis (Rehberger P et al. (2009) *Acta Derm Venereol.* 89(3):245-9.). It has been shown that an agonist of the IP receptor can reduce severity, frequency, and duration of Raynaud's attacks in patients with systemic sclerosis (Torlay et al. (1991) *Ann Rheum Dis* 50, 800-804). It has been shown that an agonist of the IP receptor can improve portal hemodynamics in patients with systemic sclerosis and Raynaud's phenomenon (Zardi et al. (2006) *In Vivo* 20(3):377-80). It has been shown that an agonist of the IP receptor can inhibit the progression of pancreatic fibrosis in obese Zucker rats (Sato et al. (2010) *Diabetes* 59(4):1092-100).

The IP receptor agonists disclosed herein provide beneficial anti-fibrotic effects to patients suffering from fibrosis of the kidney, heart, lung, skin, pancreas and liver which can be idiopathic or secondary to chronic inflammation and systemic sclerosis, for example, and are not limited to the indications described above.

In addition, there is substantial evidence that an agonist of the IP receptor can improve kidney function in acute and chronic renal failure. It has been shown that an agonist of the IP receptor can restore kidney function in endotoxemia-related acute renal failure (Johannes T et al. (2009) *Crit. Care Med.* 37(4):1423-32). It has been shown that an agonist of the IP receptor can improve renal function in a model of renal ischemia/reperfusion injury Sahsivar M O et al. (2009) *Shock* 32(5):498-502). It has been shown that an agonist of the IP receptor can prevent contrast agent-induced nephropathy in patients with renal dysfunction undergoing cardiac surgery (Spargias K et al. (2009) *Circulation* 3; 120(18):1793-9.) It has been shown that an agonist of the IP receptor can improve renal function, reduce inflammation and sclerotic changes of the kidney in a model for diabetic nephropathy Watanabe M et al. (2009) *Am J. Nephrol.* 2009; 30(1):1-11).

The IP receptor agonists disclosed herein provide beneficial improvement of renal function in patients with acute and chronic kidney injury and nephropathies secondary to dye-contrast agents, ischemia-reperfusion injury, systemic inflammation and diabetes for example, and are not limited to the indications described above.

There is considerable evidence for a causal role of Prostacyclin deficiency in the development of preeclampsia (Mills J L et al. (1999) *JAMA* 282: 356-362; Walsh S W (2004) *Prostaglandins Leukot Essent Fatty Acids* 70: 223-232). The administration of an agonist of the IP receptor has been shown to lower blood pressure in a rat model of preeclampsia (Zlatnik M G et al. (1999) *Am J Obstet. Gynecol.* 180(5):1191-5).

The IP receptor agonists disclosed herein provide beneficial improvement of hemodynamics in patients with preeclampsia.

The IP receptor agonist disclosed herein may provide beneficial treatment of cystic fibrosis.

The IP receptor agonists disclosed herein may provide chemoprevention. Chemoprevention is the practice of using of drugs, vitamins, or nutritional supplements to reduce the risk of developing, or having a recurrence of cancer. Oral iloprost (Ventavis), an analogue of prostacyclin, shows promise as a chemopreventive agent for lung cancer. Data supporting IP receptor agonist chemoprevention was presented by Paul Bunn Jr. MD, who is the executive Director of the International Association for the Study of Lung Cancer at the American Association for Cancer Research 102nd Annual Meeting showed that it significantly improved endobronchial dysplasia in former smokers.

Combinations

The compounds as defined in the first aspect or embodiments (i)-(vii) of the first aspect are also useful as co-therapeutic agents for use in combination with second agents, such as organic nitrates and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO- and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In particular, an embodiment of this invention is a pharmaceutical combination comprising a compound of formula I and a second agent wherein the second agent is a PDEV inhibitor or neutral endopeptidase inhibitor.

The compounds as defined in the first aspect or embodiments (i)-(vii) of the first aspect may be mixed with a second agent in a fixed pharmaceutical composition or it may be administered separately, before, simultaneously with or after the other drug substance.

Accordingly, the invention includes as a further aspect a combination of an IP receptor activity with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the IP receptor agonist and the further drug substance may be in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of IP receptor agonist with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-aminium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, for example corticosteroids. Suitable steroids include budesonide, beclamethasone (e.g., dipropionate), butixocort (e.g., propionate), CHF5188, ciclesonide, dexamethasone, flunisolide, fluticasone (e.g., propionate or furoate), GSK-685698, GSK-870086, LAS40369, methyl prednisolone, mometasone (e.g., furoate), prednisolone, rofleponide, and triamcinolone (e.g., acetonide). In certain preferred embodiments the steroid is long-acting corticosteroids such as budesonide, ciclesonide, fluticasone or mometasone.

Suitable second active ingredients include $\beta_2$-agonists. Suitable $\beta_2$-agonists include arformoterol (e.g., tartrate), albuterol/salbutamol (e.g., racemate or single enantiomer such as the R-enantiomer, or salt thereof especially sulfate), AZD3199, bambuterol, BI-171800, bitolterol (e.g., mesylate), carmoterol, clenbuterol, etanterol, fenoterol (e.g., racemate or single enantiomer such as the R-enantiomer, or salt thereof especially hydrobromide), flerbuterol, formoterol (e.g., racemate or single diastereomer such as the R,R-diastereomer, or salt thereof especially fumarate or fumarate dihydrate), GSK-159802, GSK-597901, GSK-678007, indacaterol (e.g., racemate or single enantiomer such as the R-enantiomer, or salt thereof especially maleate, acetate or xinafoate), LAS100977, metaproterenol, milveterol (e.g., hydrochloride), naminterol, olodaterol (e.g., racemate or single enantiomer such as the R-enantiomer, or salt thereof especially hydrochloride), PF-610355, pirbuterol (e.g., acetate), procaterol, reproterol, salmefamol, salmeterol (e.g., racemate or single enantiomer such as the R-enantiomer, or salt thereof especially xinafoate), terbutaline (e.g., sulfate) and vilanterol (or a salt thereof especially trifenatate. In certain preferred embodiments the $\beta_2$-agonist is an ultra-long-acting $\beta_2$-agonist such as indacaterol, or potentially carmoterol, LAS-100977, milveterol, olodaterol, PF-610355 or vilanterol. A preferred embodiment one of the second active ingredients is indacaterol (i.e. (R)-5-[2-(5,6-diethyl-indan-2-ylamino)-1-hydroxyethyl]-8-hydroxy-1H-quinolin-2-one) or a salt thereof. This is a $\beta_2$-adrenoceptor agonist that has an especially long duration of action (i.e. over 24 hours) and a short onset of action (i.e. about 10 minutes). This compound is prepared by the processes described in international patent applications WO 2000/75114 and WO 2005/123684. It is capable of forming acid addition salts, particularly pharmaceutically acceptable acid addition salts. A preferred salt of (R)-5-[2-(5,6-diethyl-indan-2-ylamino)-1-hydroxyethyl]-8-hydroxy-1H-quinolin-2-one is the maleate salt. Another preferred salt is (R)-5-[2-(5,6-diethyl-indan-2-ylamino)-1-hydroxyethyl]-8-hydroxy-1H-quinolin-2-one acetate. Another preferred salt is (R)-5-[2-(5,6-diethyl-indan-2-ylamino)-1-hydroxyethyl]-8-hydroxy-1H-quinolin-2-one xinafoate.

Suitable bronchodilatory drugs include anticholinergic or antimuscarinic agents, such as aclidinium (e.g., bromide), BEA-2108 (e.g., bromide), BEA-2180 (e.g., bromide), CHF-5407, darifenacin (e.g., bromide), darotropium (e.g., bromide), glycopyrrolate (e.g., racemate or single enantiomer, or salt thereof especially bromide), dexpirronium (e.g., bromide), iGSK-202405, GSK-203423, GSK-573719, GSK-656398, ipratropium (e.g., bromide), LAS35201, LAS186368, otilonium (e.g., bromide), oxitropium (e.g., bromide), oxybutynin, PF-3715455, PF-3635659, pirenzepine, revatropate (e.g., hydrobromide), solifenacin (e.g., succinate), SVT-40776, TD-4208, terodiline, tiotropium (e.g., bromide), tolterodine (e.g., tartrate), and trospium (e.g., chloride). In certain preferred embodiments the muscarinic antagonists is long-acting muscarinic antagonist such as darotropium bromide, glycopyrrolate or tiotropium bromide.

Suitable dual anti-inflammatory and bronchodilatory drugs include dual beta-2 adrenoceptor agonist/muscarinic antagonists such as GSK-961081 (e.g., succinate) and those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Accordingly, the invention includes as a further aspect a combination of IP receptor agonist with agents that inhibit ALK5 and/or ALK4 phosphorylation of Smad2 and Smad3.

Accordingly, the invention includes as a further aspect a combination of IP receptor agonist with second agents that are Rho-kinase inhibitors.

Accordingly, the invention includes as a further aspect a combination of IP receptor agonist with second agents that are tryptophan hydroylase 1 (TPH1) inhibitors.

Accordingly, the invention includes as a further aspect a combination of IP receptor agonist with second agents that are multi-kinase inhibitors, such as imatinib mysilate, Gleevec. Imatinib functions as a specific inhibitor of a number of tyrosine kinase enzymes. It occupies the TK active site, leading to a decrease in activity. TK enzymes in the body include the insulin receptor. Imatinib is specific for the TK domain in the Abelson proto-oncogene, c-kit and PDGF-R (platelet-derived growth factor receptor).

In an embodiment of this invention, the IP receptor agonist of this invention are dosed in combination with a second active agent selected from phosphodiesterase V inhibitors, neutral endopeptidase 1 inhibitors, THP1 inhibitors, multi-kinase inhibitors, endothelin antagonist, diuretic, aldosteron receptor blocker, and endothelin receptor blocker. In an embodiment of this invention, the IP receptor agonist of this invention are dosed in combination with a second active agent selected from phosphodiesterase V inhibitors, neutral endopeptidase 1 inhibitors, THP1 inhibitors, and multi-kinase inhibitors, such as PDGFR or c-Kit.

The invention is illustrated by the following Examples.

EXAMPLES

Preparation of 7-(2,3-Di-p-tolyl-7,8-dihydropyrido[2,3-b]pyrazin-5(6H)-yl)heptanoic acid

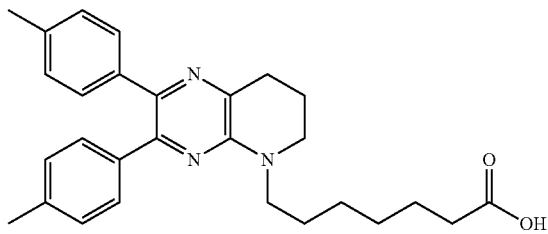 [SMILES: Cc1ccc(-c2nc3c(nc2-c2ccc(C)cc2)N(CCCCCCC(=O)O)CCC3)cc1]

Step 1: Ethyl 7-(2,3-dip-tolyl-7,8-dihydropyrido[2,3-b]pyrazin-5(6H)-yl)heptanoate To a solution of 2,3-Di-p-tolyl-5,6,7,8-tetrahydropyrido[2,3-b]pyrazine (Intermediate E) (10 g, 31.7 mmol) in DCE (300 ml) was added DIPEA (6.09 ml, 34.9 mmol) followed by ethyl 7-oxoheptanoate (10.92 g, 63.4 mmol). The mixture was stirred at RT for 10 minutes and sodium triacetoxyborohydride (16.80 g, 79 mmol) was added portionwise. The reaction mixture was heated at 40° C. overnight and then added slowly to water (500 ml) and stirred at RT for 10 minutes. The organic layer was separated and the aqueous layer extracted with dichloromethane (2×200 ml). The combined organics were washed with brine (200 ml), dried over anhydrous sodium sulfate and concentrated in vacuo to give a pale yellow oil. Isolute Separtis SCX-2 (capture/release super cation exchange resin) (222 g, 127 mmol) was added to a column and the product was loaded with MeOH (50 ml). The column was flushed with MeOH (750 L) followed by 2 N NH$_3$/MeOH (1000 ml, prepared from 280 ml 7 N+720 ml MeOH) to afford the title compound. No further purification was carried out; HPLC (Agilent 1200) Rt 6.38 min, Method B

Step 2: 7-(2,3-di-p-tolyl-7,8-dihydropyrido[2,3-b]pyrazin-5(6H)-yl)heptanoic acid Ethyl 7-(2,3-di-p-tolyl-7,8-dihydropyrido[2,3-b]pyrazin-5(6H)-yl)heptanoate (step 1) was dissolved in THF (94 ml) and lithium hydroxide monohydrate (7.79 g, 186 mmol) in water (94 ml) was added dropwise. The reaction mixture was warmed to 50° C. and stirred for 7.5 hours. The reaction mixture was concentrated in vacuo to remove the THF and diluted with water (500 ml). The pH of the aqueous layer was adjusted to pH 2 with 1 N HCl (100 ml) and extracted with EtOAc (3×500 ml). The combined organic layers were washed with brine (200 ml), dried over anhydrous sodium sulfate and concentrated in vacuo. The crude solid was suspended in TBME/hexane (1:1, 100 ml) and rotated on the rotary evaporator (no vacuum) at RT until crystals formed. The solid was removed by filtration, washed with heptane (50 ml) and dried at RT overnight. The solid was re-crystallized from a hot mixture of EtOH (211 ml) and water (159 ml). After seeding and stirring for 1 h at 5° C., the crystals were filtered off and the product dried overnight at 40° C. in a vacuum oven to afford the title compound;

Characterising data: Rt=4.54 mins; [M+H]$^+$444.4, Method 10 minLC_v003

$^1$H NMR (400 MHz, DMSO-d6) δ 11.95 (1H, br s), 7.21 (2H, d), 7.13 (2H, d), 7.07 (2H, d), 7.03 (2H, d), 3.57 (2H, m), 3.44 (2H, m), 2.88 (2H, t), 2.27 (3H, s), 2.26 (3H, s), 2.15 (2H, t), 2.00 (2H, m), 1.59 (2H, m), 1.47 (2H, m), 1.36-1.25 (4H, m).

Preparation of 2,3-Di-p-tolyl-5,6,7,8-tetrahydropyrido[2,3-b]pyrazine (Intermediate E)

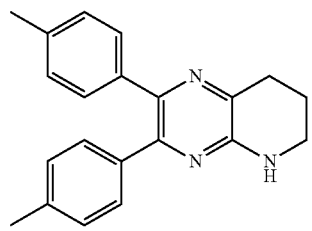 [SMILES: Cc1ccc(-c2nc3c(nc2-c2ccc(C)cc2)NCCC3)cc1]

Step 1: 2,3-Di-p-tolylpyrido[2,3-b]pyrazine

A solution of 1,2-dip-tolylethane-1,2-dione (commercially available) (175 g, 733 mmol) and pyridine-2,3-diamine (80 g, 733 mmol) in EtOH (1609 ml) and AcOH (179 ml) was heated to reflux (bath at 85° C.) for 1.5 h. The mixture was allowed to cool and concentrated in vacuo. The crude material was dissolved in DCM (500 ml) and filtered through silica to remove baseline impurities. The silica was washed with EtOAc (2 L). The combined filtrate layers were concentrated in vacuo to give a brown solid. The material was triturated in 1:1 TBME/heptane (300 ml). The solid was removed by filtration and washed with 1:1 TBME/heptane (200 ml) before drying at RT over 2 days to afford the title compound as an AcOH salt (1 eq).

HPLC (Agilent 1200), Rt 5.37 min, Method B.

Step 2: 2,3-Di-p-tolyl-5,6,7,8-tetrahydropyrido[2,3-b]pyrazine

A solution of 2,3-dip-tolylpyrido[2,3-b]pyrazine (step 1) (181 g, 487 mmol) in EtOH/THF (1:2, 2100 ml) was treated with 10% palladium on carbon (30 g, 28.8 mmol) and the reaction mixture was placed under 0.1 bar of hydrogen at RT. After 2 days and 4 days respectively, additional batches of 10% palladium on carbon (10 g, 9.6 mmol, twice) were added along with Et$_3$N (85 ml, 706 mmol, twice). After 7 days in total, the reaction mixture was filtered through Hyflo (filter material) and washed through with THF (2.5 L in portions). The filtrate was concentrated in vacuo to give a green/yellow solid. The solid was triturated with 1:1 TBME/heptane (500 ml) and filtered. The solid was washed with 1:1 TBME/heptane (200 ml) to give a pale yellow solid which was dried overnight to afford the title compound; HPLC (Agilent 1200), Rt 4.73 min, Method B.

General Conditions

Mass spectra were run on LCMS systems using electrospray ionization. These were either Agilent 1100 HPLC/Micromass Platform Mass Spectrometer combinations or Waters Acquity UPLC with SQD Mass Spectrometer. [M+H]$^+$ refers to mono-isotopic molecular weights. NMR spectra were run on open access Bruker AVANCE 400 NMR spectrometers using ICON-NMR. Spectra were measured at 298K and were referenced using the solvent peak. The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined below, the terms have their generally accepted meanings.

Analytical HPLC Conditions for Method B
Column: Zorbax Eclipse XDB-C18 4.6×50 mm, 1.8 μm
Column Temperature: 35° C.
Eluents: A: $H_2O$+0.1% TFA, B: acetonitrile+0.1% TFA
Flow Rate: 1 ml/min
Gradient: 5-100% MeCN (6 min), 100 MeCN (1.5 min), 100-5% MeCN (0.5 min)
Analytical HPLC Conditions for Method 10 minLC_v003
Column: Waters BEH C18 50×2.1 mm, 1.7 μm
Column Temperature: 50° C.
Eluents: A: $H_2O$, B: acetonitrile, both containing 0.1% TFA
Flow Rate: 0.8 ml/min
Gradient: 0.20 min 5% B; 5% to 95% B in 7.80 min, 1.00 min 95% B

ABBREVIATIONS

AcOH acetic acid
br broad
d doublet
DCM dichloromethane
DCE 1,2-dichloroethane
DIPEA Diisopropylethylamine
EtOAc ethyl acetate
EtOH ethanol
h hour(s)
HPLC high pressure liquid chromatography
IT internal temperature (of the mixture in the reactor)
JT jacket temperature (temperature of liquid in the cooling/heating jacket of the reactor)
LC-MS liquid chromatography and mass spectrometry
MeOH methanol
MS mass spectrometry
m multiplet
min minutes
ml milliliter(s)
NMR nuclear magnetic resonance
NMP 1-Methyl-2-pyrrolidone
Rt retention time
RT room temperature (about 22-26° C.)
s singlet
t triplet
TBME methyl-tert-butyl ether
THF tetrahydrofuran
$w_{theoretical}$ theoretically calculated mass fraction of the respective elements based on the chemical formula (given in % m/m)
$w_{measured}$ experimentally measured mass fraction of the respective element (given in % m/m)

Example 1

Preparation of the sulfuric acid salt of 7-(2,3-di-p-tolyl-7,8-dihydropyrido[2,3-b]pyrazin-5(6H)-yl) heptanoic acid

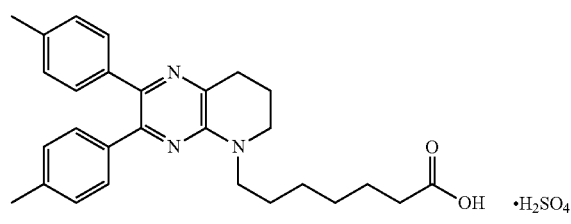

Preparation of the Sulfuric Acid Salt—Batch A
54.40 mg 7-(2,3-di-p-tolyl-7,8-dihydropyrido[2,3-b]pyrazin-5(6H)-yl)heptanoic acid (0.123 mmol) and 11.66 mg sulfuric acid (0.117 mmol, added as 98%-solution) were dissolved in 1 mL hot acetonitrile. While shaking with 250 rpm, the solution was cooled to RT. Spontaneous crystallization occurred during cooling and a yellow suspension was obtained. The suspension was filtered and the filter cake was dried at RT overnight. Yield: 30 mg yellow powder.

Preparation of the Sulfuric Acid Salt—Batch B
700 mg (1.578 mmol) 7-(2,3-di-p-tolyl-7,8-dihydropyrido[2,3-b]pyrazin-5(6H)-yl)heptanoic acid was suspended in 8 mL acetone in a 50 mL four-necked flask with paddle stirrer at RT and was heated at IT 40° C., JT 60° C. (pH 5). 157 mg (1.578 mmol) sulfuric acid 98% was added (pH 1, clear intensive yellow solution). The clear solution was cooled down to RT over 30 min. Crystallization took place spontaneously and quickly at 40° C. The suspension was stirred at RT overnight (16 h). An intensive yellow suspension was obtained. The suspension was filtered at RT using a glass filter (fast filtration, duration: <0.5 min.) and the filter cake was washed with 3×1.0 mL pure acetone. The wet filter cake was dried to dryness in a drying oven in two steps: first, at RT overnight (16 h) and, afterwards, at 50° C. overnight (16 h). Yield: 812 mg yellow powder.

X-Ray Powder Diffraction Pattern of the Salt from Batch B
An x-ray powder diffraction pattern was recorded on a Bruker™ D8 diffractometer using CuKα radiation. The X-ray diffraction pattern thus determined is shown in FIG. 1 and represented in Table 1A below by the reflection lines and intensities of the most important lines.

TABLE 1A

| Angle [2-Theta°] | d value [Angstrom] | Intensity [%] |
|---|---|---|
| 5.8 | 15.15493 | 29 |
| 6.8 | 12.94921 | 100 |
| 9.4 | 9.36791 | 59 |
| 13.7 | 6.45750 | 19 |
| 16.8 | 5.27041 | 31 |
| 17.0 | 5.19691 | 34 |
| 17.7 | 5.00591 | 17 |
| 18.4 | 4.80930 | 31 |
| 19.5 | 4.54719 | 19 |
| 20.7 | 4.28743 | 25 |
| 22.1 | 4.02451 | 78 |
| 22.6 | 3.93143 | 27 |

TABLE 1A-continued

| Angle [2-Theta°] | d value [Angstrom] | Intensity [%] |
| --- | --- | --- |
| 23.5 | 3.77811 | 18 |
| 24.3 | 3.66109 | 22 |
| 25.0 | 3.55941 | 22 |
| 26.4 | 3.37394 | 19 |
| 26.7 | 3.33865 | 17 |
| 27.5 | 3.24543 | 19 |
| 28.2 | 3.16425 | 16 |
| 31.6 | 2.83061 | 16 |

Elemental Analysis of the Salt from Batch B

The results of elemental analysis are given in Table 1B below.

Water content (Karl-Fischer titration): <0.2% m/m

TABLE 1B

| Element | $w_{theoretical}$ [% m/m] | $w_{measured}$ [% m/m] |
| --- | --- | --- |
| C | 62.09 | 61.90 |
| H | 6.51 | 6.61 |
| N | 7.76 | 7.70 |
| S | 5.92 | 5.72 |
| O | 62.09 | 17.80 |

Experimental data corresponded well to expectations for the stoichiometric formula $C_{28}H_{33}N_3O_2 \cdot H_2SO_4$.

Melting Point of the Salt from Batch B

Measured on a Büchi Melting Point Apparatus: ~190° C. (visual determination)

pH of a 1% Solution/Suspension in Water: 1.78 (24.4° C.)

A mixture of 10 mg salt and 1 mL water was treated about 5 min with ultrasound. Afterwards, the mixture was stirred for one hour at RT followed by pH measurement.

Differential Scanning Calorimetry (DSC) Data

Data were measured using a Perkin Elmer Diamond DSC instrument. Sample preparation was done in an aluminium crucible with micro holes. A heating rate of 20 K/min was applied and the sample was heated-from 30 to 210° C. The DSC curve shows some pre-melting events that are likely attributable to a polymorphic behavior of the sulfuric acid salt. An interpretation of the thermal events is given below.

The first double-endotherm with an onset temperature of 141.3° C. corresponds to a (partial) melting of the sample that is characterized by the XRPD given in FIG. 1. The subsequently following exotherm (onset temperature of 153.5° C.) likely represents the recrystallization of a more stable crystalline form that finally melts at 190.0° C. (onset temperature of final melting endotherm).

Example 2

Preparation of the xinafoic acid salt of (7-(2,3-di-p-tolyl-7,8-dihydropyrido[2,3-b]pyrazin-5(6H)-yl) heptanoic acid

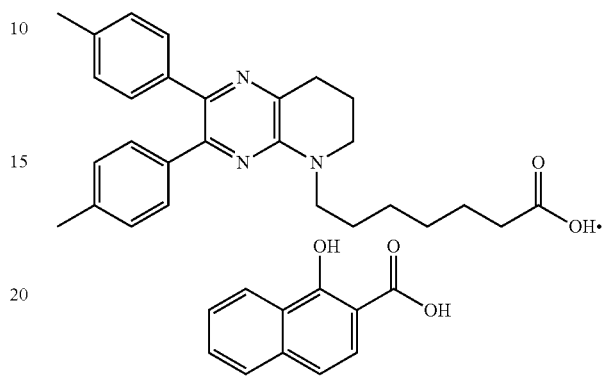

Preparation of the Xinafoic Acid Salt—Batch A 45.50 mg 7-(2,3-di-p-tolyl-7,8-dihydropyrido[2,3-b] pyrazin-5(6H)-yl)heptanoic acid (0.103 mmol) and 18.58 mg 1-hydroxy-2-naphthoic acid (0.097 mmol) were dissolved in 1 mL hot acetonitrile. While shaking with 250 rpm, the solution was cooled to RT. Spontaneous crystallization occurred during cooling and a yellow suspension was obtained. The suspension was filtered and the filter cake was dried at RT overnight. Yield: 50 mg yellow powder.

Preparation of the Xinafoic Acid Salt—Batch B 600 mg (1.353 mmol) 7-(2,3-di-p-tolyl-7,8-dihydropyrido [2,3-b]pyrazin-5(6H)-yl)heptanoic acid was suspended in 8 mL acetonitrile and 1 mL acetone in a 50 mL four-necked flask with paddle stirrer at RT and was heated and dissolved at IT 50° C., JT 65° C. (pH 5). 260 mg (1.353 mmol) xinafoic acid was added (pH 3, clear solution). The clear solution was cooled down to RT over 30 min (crystallization took place at IT 43° C.) and was then stirred at RT overnight (16 h). A yellow suspension was obtained. The suspension was filtered at RT using a glass filter (fast filtration, duration: <0.5 min.) and the filter cake was washed with 3×1.0 mL pure acetonitrile. The resulting wet filter cake was dried to dryness in a drying oven at RT overnight (16 h). Yield: 709 mg yellow powder.

X-Ray Powder Diffraction Pattern of the Xinafoic Acid Salt from Batch B

Figure 2:
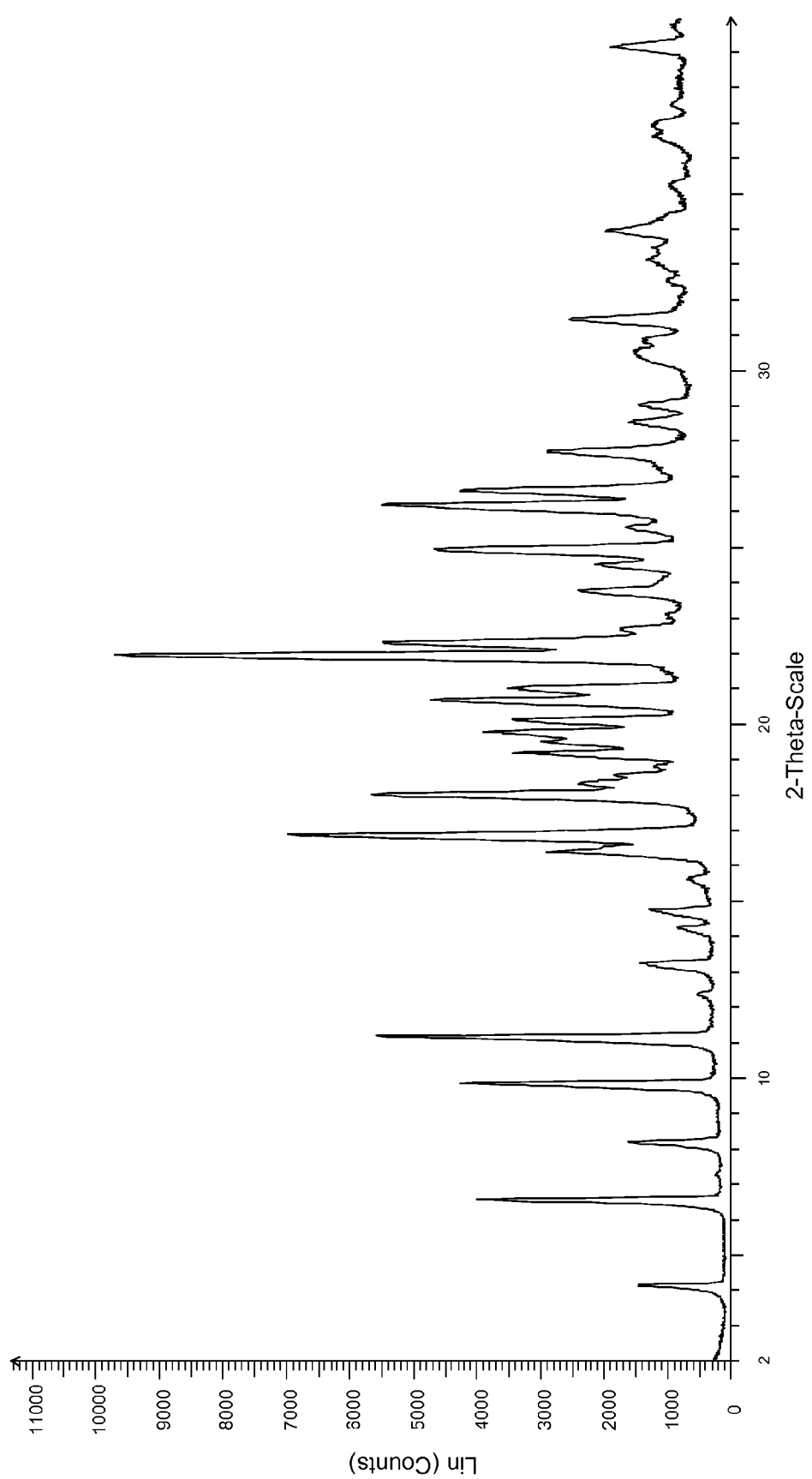
FIG. 2 is an x-ray powder diffraction pattern of the crystalline xinafoic acid salt of 7-(2,3-di-p-tolyl-7,8-dihydropyrido[2,3-b]pyrazin-5(6H)-yl)heptanoic acid.

An x-ray powder diffraction pattern was recorded on a Bruker™ D8 diffractometer using CuKα radiation. The X-ray diffraction pattern thus determined is shown in FIG. 2 and represented in Table 2A below by the reflection lines and intensities of the most important lines.

TABLE 2A

| Angle [2-Theta°] | d value [Angstrom] | Intensity [%] |
| --- | --- | --- |
| 4.1 | 21.59159 | 15 |
| 6.5 | 13.54085 | 42 |
| 8.2 | 10.83561 | 17 |

TABLE 2A-continued

| Angle [2-Theta°] | d value [Angstrom] | Intensity [%] |
|---|---|---|
| 9.8 | 8.99261 | 44 |
| 11.1 | 7.93208 | 58 |
| 13.2 | 6.70069 | 14 |
| 16.4 | 5.40275 | 30 |
| 16.9 | 5.25749 | 73 |
| 18.0 | 4.92360 | 59 |
| 18.3 | 4.83870 | 25 |
| 18.5 | 4.78748 | 18 |
| 18.8 | 4.71687 | 13 |
| 19.2 | 4.62547 | 34 |
| 19.5 | 4.54879 | 31 |
| 19.8 | 4.48858 | 41 |
| 20.1 | 4.41533 | 35 |
| 20.7 | 4.29502 | 49 |
| 21.0 | 4.22564 | 36 |
| 21.9 | 4.04780 | 100 |
| 22.3 | 3.98336 | 57 |
| 22.7 | 3.91795 | 18 |
| 23.8 | 3.74177 | 25 |
| 24.5 | 3.63050 | 21 |
| 24.9 | 3.56760 | 48 |
| 25.6 | 3.48139 | 17 |
| 26.2 | 3.39982 | 57 |
| 26.6 | 3.34736 | 44 |
| 27.7 | 3.21607 | 30 |
| 28.5 | 3.12457 | 17 |
| 29.0 | 3.07297 | 15 |
| 30.5 | 2.92594 | 16 |
| 31.5 | 2.84205 | 26 |
| 34.0 | 2.63707 | 20 |
| 39.2 | 2.29747 | 20 |

Elemental Analysis of the Xinafoic Acid Salt from Batch B
The results of elemental analysis are given in Table 2B below.
Water content (Karl-Fischer titration): <0.2% m/m

TABLE 2B

| Element | $w_{theoretical}$ [% m/m] | $w_{measured}$ [% m/m] |
|---|---|---|
| C | 74.15 | 73.75 |
| H | 6.54 | 6.49 |
| N | 6.65 | 6.69 |
| O | 12.66 | 12.74 |

Experimental data corresponded well to expectations for the stoichiometric formula $C_{28}H_{33}N_3O_2 \cdot C_{11}H_8O_3$.

Melting Point of the Xinafoic Acid Salt from Batch B
Measured on a Büchi Melting Point Apparatus: ~153° C. (visual determination)

pH of a 1% Solution/Suspension in Water: 6.46 (24.5° C.)
A mixture of 10 mg salt and 1 mL water was treated about 5 min with ultrasound. Afterwards, the mixture was stirred for one hour at RT followed by pH measurement.

Differential Scanning Calorimetry (DSC) Data:
Data were measured using a Perkin Elmer Diamond DSC instrument. Sample preparation was done in an aluminium crucible with micro holes. A heating rate of 20 K/min was applied and the sample was heated from 30 to 175° C. The DSC curve shows some pre-melting events that are likely attributable to a polymorphic behavior of the xinafoic acid salt. The first endotherm with an onset temperature of 143.7° C. corresponds to a (partial) melting of the sample that is characterized by the XRPD given in FIG. 2. The subsequently following exotherm (onset temperature of 147.1° C.) likely represents the recrystallization of a more stable crystalline form that finally melts at 153.5° C. (onset temperature of final melting endotherm).

SC-XRD (single crystal X-ray diffraction) data showed that the xinafoate salt is a co-crystal and not a salt (no proton transfer).

Example 3

Preparation of the Sodium Salt of (7-(2,3-di-p-tolyl-7,8-dihydropyrido[2,3-b]pyrazin-5(6H)-yl)heptanoic acid

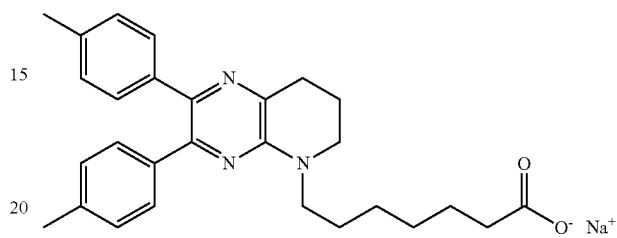

Preparation of the Sodium Salt—Batch A
54.70 mg 7-(2,3-di-p-tolyl-7,8-dihydropyrido[2,3-b]pyrazin-5(6H)-yl)heptanoic acid (0.114 mmol) and 14.48 mg sodium hydroxide (0.114 mmol, added as 30%-solution in water) were dissolved in 1 mL hot acetonitrile. While shaking with 250 rpm, the solution was cooled to RT. Spontaneous crystallization occurred during cooling and a white suspension was obtained. The suspension was filtered at RT and the filter cake was dried at RT overnight. Yield: 48 mg white powder.

Preparation of the Sodium Salt—Batch B
800 mg (1.804 mmol) 7-(2,3-di-p-tolyl-7,8-dihydropyrido[2,3-b]pyrazin-5(6H)-yl)heptanoic acid was suspended in 8 mL acetonitrile and 1.5 mL acetone in a 50 mL four-necked flask with paddle stirrer at RT and was heated at IT 55° C., JT 70° C. (pH 5). 241 mg (1.804 mmol) NaOH 30% was added (pH 10, clear solution). The solution was cooled down to RT over 30 min and crystallization took place quickly during cooling resulting in a very thick suspension. The suspension was diluted with 4 mL acetonitrile and stirred at RT overnight (16 h). A very thick white-grey suspension was obtained. The suspension was filtered at RT using a glass filter (slow but good filtration, duration: <3 min.) and the filter cake was washed with 3×3.0 mL pure acetonitrile. The wet filter cake was dried to dryness in a drying oven at RT overnight (16 h). Yield: 810 mg white powder.

Figure 3:
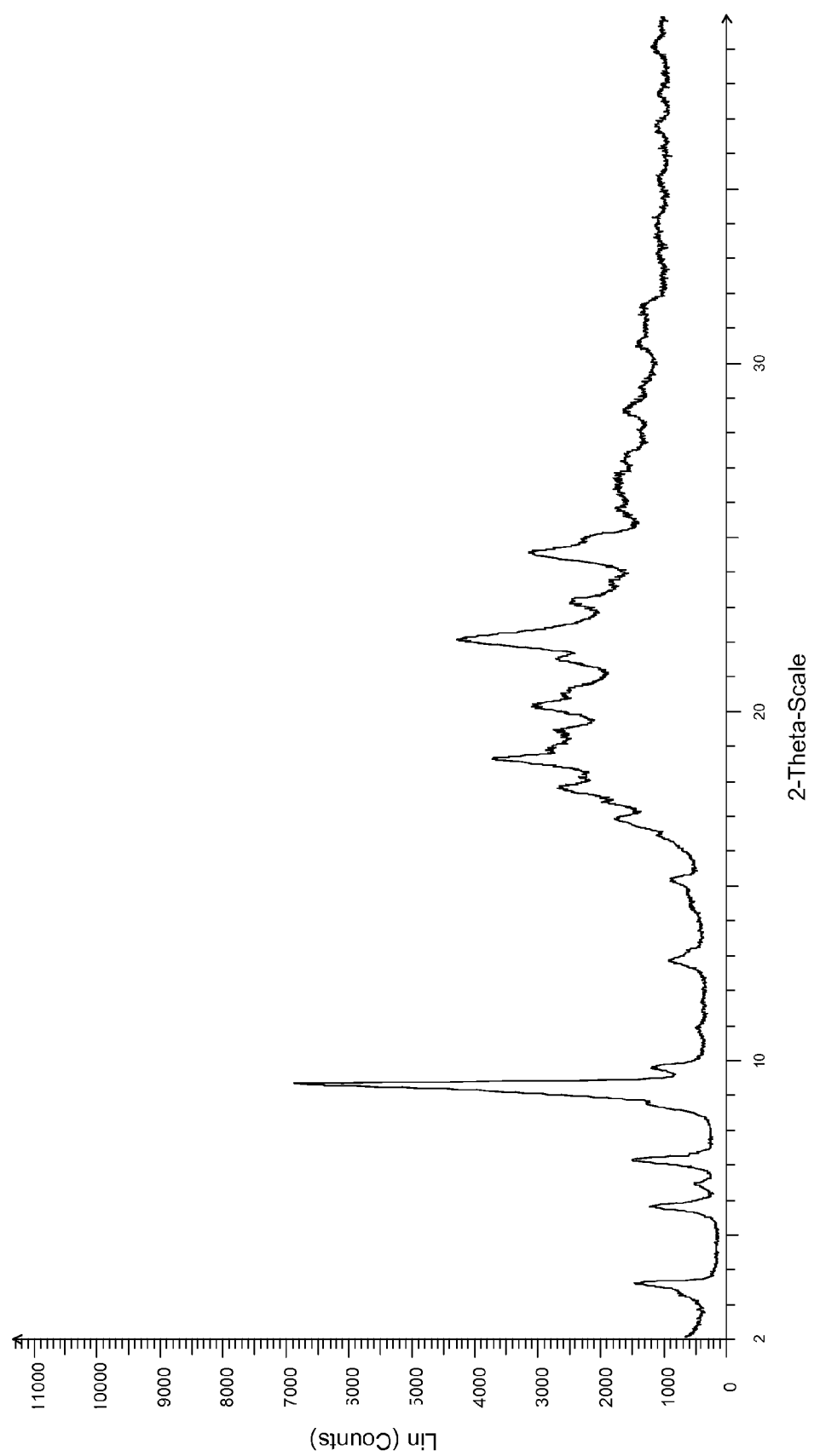
FIG. 3 is an x-ray powder diffraction pattern of the crystalline sodium salt of 7-(2,3-di-p-tolyl-7,8-dihydropyrido[2,3-b]pyrazin-5(6H)-yl)heptanoic acid.

X-Ray Powder Diffraction Pattern of the Sodium Salt from Batch B
An x-ray powder diffraction pattern was recorded on a Bruker™ D8 diffractometer using CuKα radiation. The X-ray diffraction pattern thus determined is shown in FIG. 3 and represented in Table 3A below by the reflection lines and intensities of the most important lines.

TABLE 3A

| Angle [2-Theta°] | d value [Angstrom] | Intensity [%] |
|---|---|---|
| 3.6 | 24.76048 | 21 |
| 5.8 | 15.29105 | 18 |
| 7.1 | 12.41300 | 22 |
| 8.7 | 10.18755 | 18 |
| 9.3 | 9.51795 | 100 |
| 9.8 | 9.03500 | 17 |
| 12.8 | 6.88567 | 13 |

TABLE 3A-continued

| Angle [2-Theta°] | d value [Angstrom] | Intensity [%] |
|---|---|---|
| 15.2 | 5.83606 | 13 |
| 16.4 | 5.38580 | 16 |
| 16.9 | 5.23665 | 26 |
| 17.4 | 5.08948 | 29 |
| 17.8 | 4.97591 | 39 |
| 18.6 | 4.75516 | 54 |
| 18.9 | 4.68256 | 42 |
| 19.4 | 4.56045 | 39 |
| 20.2 | 4.39926 | 44 |
| 20.5 | 4.32902 | 38 |
| 21.5 | 4.12556 | 39 |
| 22.1 | 4.02497 | 62 |
| 23.2 | 3.83538 | 36 |
| 23.7 | 3.74884 | 27 |
| 24.6 | 3.62295 | 45 |
| 25.0 | 3.56547 | 34 |

Elemental Analysis of the Sodium Salt from Batch B

The results of elemental analysis are given in Table 3B below.

Water content (Karl-Fischer titration): 2.8% m/m

TABLE 3B

| Element | $w_{theoretical}$ [% m/m] (considering 2.8% water content) | $w_{measured}$ [% m/m] |
|---|---|---|
| C | 70.23 | 69.83 |
| H | 7.05 | 7.25 |
| N | 8.77 | 8.95 |
| O | 9.15 | 9.15 |
| Na | 4.80 | 4.65 |

Experimental data corresponded well to expectations for the stoichiometric formula $C_{28}H_{32}N_3O_2Na$ considering an additional water content of 2.8%.

Melting Point of the Sodium Salt from Batch B

Measured on a Büchi Melting Point Apparatus: ~272° C. (visual determination)

pH of a 1% Solution/Suspension in Water: 9.16 (24.3° C.)

A mixture of 10 mg salt and 1 mL water was treated about 5 min with ultrasound. Afterwards, the mixture was stirred for one hour at RT followed by pH measurement.

Differential Scanning Calorimetry (DSC) Data:

Data were measured using a Perkin Elmer Diamond DSC instrument. Sample preparation was done in an aluminium crucible with micro holes. A heating rate of 20 K/min was applied and the sample was heated from 30 to 290° C. The DSC curve shows some pre-melting events that are likely attributable to a polymorphic behavior of the sodium salt. The first endotherm with an onset temperature of 136.7° C. corresponds to a (partial) melting of the sample that is characterized by the XRPD given in FIG. 3. The subsequently following exotherm (onset temperature of 148.6° C.) likely represents the recrystallization of a more stable crystalline form that finally melts at 220.3° C. (onset temperature of final melting endotherm).

Example 4

Preparation of the Hydrogen Chloride Salt of (7-(2, 3-di-p-tolyl-7,8-dihydropyrido[2,3-b]pyrazin-5(6H)-yl)heptanoic acid

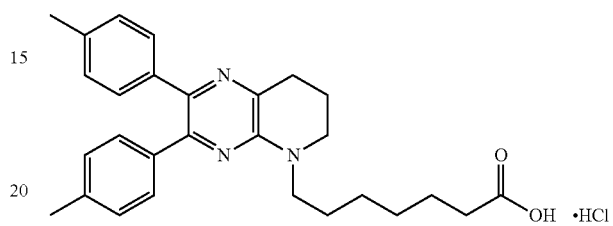

Preparation of the Hydrogen Chloride Salt—Batch A 56.00 mg 7-(2,3-di-p-tolyl-7,8-dihydropyrido[2,3-b]pyrazin-5(6H)-yl)heptanoic acid (0.126 mmol) and 11.82 mg hydrochloric acid (0.120 mmol, added as 37% solution in water) were dissolved in 1 mL hot acetonitrile. While shaking with 250 rpm, the solution was cooled to RT. The resulting clear solution was evaporated at RT and the residue was dissolved in 1 mL hot diisopropyl ether. While shaking with 250 rpm, the solution was cooled to RT and precipitation was observed. The resulting suspension was filtered and the filter cake was dried at RT overnight. Yield: 44 mg yellow powder.

Preparation of the Hydrogen Chloride Salt—Batch B

Step 1: 150.20 mg 7-(2,3-di-p-tolyl-7,8-dihydropyrido[2,3-b]pyrazin-5(6H)-yl)heptanoic acid (0.339 mmol) and 33.37 mg hydrochloric acid (0.339 mmol, added as 37%-solution in water) were dissolved in 2-3 mL hot methanol. The solution was evaporated. 0.10 mL acetone was added to the solid residue and the mixture was heated to 55° C. A clear solution was obtained and cooled to RT. The solution was seeded with material from Batch A and turned into a suspension during stirring.

Step 2: 800 mg (1.804 mmol) 7-(2,3-di-p-tolyl-7,8-dihydropyrido[2,3-b]pyrazin-5(6H)-yl)heptanoic acid was suspended in 8 mL acetone in a 50 mL four-necked flask with paddle stirrer at RT and was heated at IT 45° C., JT 60° C. (pH 5) and 180 mg (1.804 mmol) HCl 37% was added (pH 1, clear intensive yellow solution). The clear solution was cooled down to RT over 30 min and seeding was carried out at IT 30° C. with the suspension obtained in Step 1. Crystallization took place quickly and further stirring of the mixture at RT overnight (16 h) was performed resulting in a yellow suspension. The suspension was filtered at RT using a glass filter (fast filtration, duration: <0.5 min.) and the filter cake was washed with 3×1.0 mL pure acetone. The wet filter cake was dried to dryness in a drying oven at RT overnight (16 h). Yield: 693 mg intensive yellow powder.

X-Ray Powder Diffraction Pattern of the Hydrogen Chloride Salt from Batch B

Figure 4:
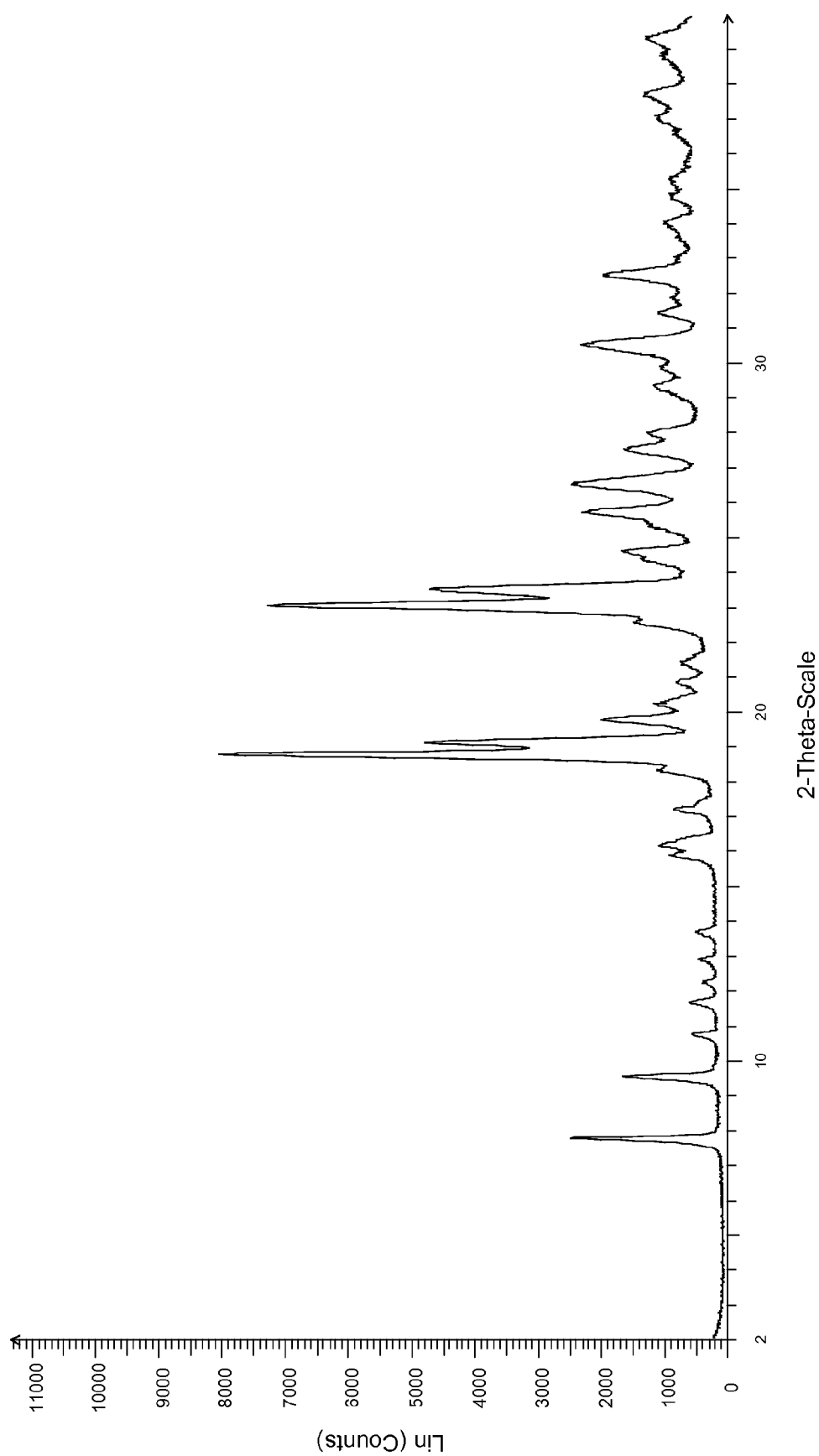
FIG. 4 is an x-ray powder diffraction pattern of the crystalline hydrogen chloride salt of 7-(2,3-di-p-tolyl-7,8-dihydropyrido[2,3-b]pyrazin-5(6H)-yl)heptanoic acid.

An x-ray powder diffraction pattern was recorded on a Bruker™ D8 diffractometer using CuKα radiation. The X-ray diffraction pattern thus determined is shown in FIG. 4 and represented in Table 4A below by the reflection lines and intensities of the most important lines.

33

TABLE 4A

| Angle [2-Theta°] | d value [Angstrom] | Intensity [%] |
|---|---|---|
| 7.7 | 11.40681 | 31 |
| 9.5 | 9.28896 | 20 |
| 15.9 | 5.57297 | 11 |
| 16.2 | 5.47587 | 13 |
| 17.2 | 5.15241 | 10 |
| 18.3 | 4.83356 | 14 |
| 18.8 | 4.71985 | 100 |
| 19.1 | 4.63678 | 60 |
| 19.8 | 4.48560 | 25 |
| 20.2 | 4.38747 | 14 |
| 22.6 | 3.93323 | 18 |
| 23.1 | 3.85245 | 90 |
| 23.5 | 3.77877 | 57 |
| 24.4 | 3.64399 | 17 |
| 24.6 | 3.61400 | 21 |
| 25.4 | 3.50649 | 15 |
| 25.7 | 3.45769 | 29 |
| 26.6 | 3.35463 | 30 |
| 27.5 | 3.23665 | 20 |
| 28.0 | 3.18357 | 16 |
| 30.6 | 2.92309 | 29 |
| 32.6 | 2.74797 | 24 |
| 37.7 | 2.38142 | 16 |
| 39.3 | 2.28914 | 16 |

Elemental Analysis of the Hydrogen Chloride Salt from Batch B
The results of elemental analysis are given in Table 4B below.
Water content (Karl-Fischer titration): <0.2% m/m

TABLE 4B

| Element | $w_{theoretical}$ [% m/m] | $w_{measured}$ [% m/m] |
|---|---|---|
| C | 70.06 | 69.91 |
| H | 7.14 | 7.10 |
| N | 8.75 | 8.77 |
| O | 6.66 | 6.91 |
| Cl | 7.39 | 7.32 |

Experimental data corresponded well to expectations for the stoichiometric formula $C_{28}H_{33}N_3O_2 \cdot HCl$.

Melting Point of the Hydrogen Chloride Salt from Batch B
Measured on a Büchi Melting Point Apparatus: ~153° C. (visual determination)

pH of a 1% Solution/Suspension in Water: 2.3 (25.2° C.)
A mixture of 10 mg salt and 1 mL water was treated about 5 min with ultrasound. Afterwards, the mixture was stirred for one hour at RT followed by pH measurement.

Differential Scanning Calorimetry (DSC) Data:
Data were measured using a Perkin Elmer Diamond DSC instrument. Sample preparation was done in an aluminium crucible with micro holes. A heating rate of 20 K/min was applied and the sample was heated from 30 to 175° C. The DSC curve shows a pre-melting endotherm (onset temperature of 94.8° C.) that is likely attributable to a polymorphic solid-solid phase transition of the HCl salt. The second endotherm (onset temperature of 147.3° C.) is related to the melting of the sample.

The invention claimed is:
1. A crystalline form of the compound:

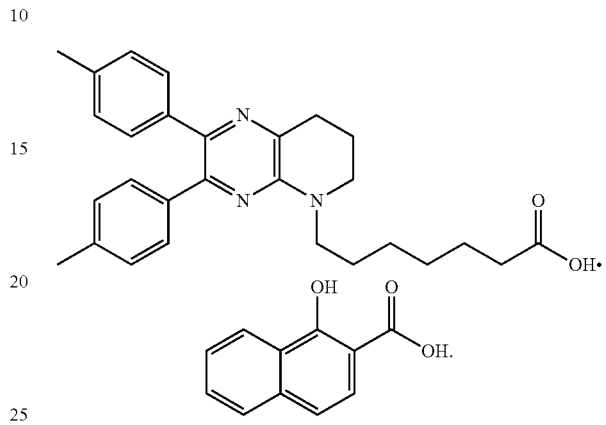

2. The crystalline form of the compound according to claim 1 which has the following characteristic diffraction lines (2θ) in the X-ray diffraction pattern thereof: 11.1°, 16.9°, 18.0°, 21.9°, 22.3° and 26.2°.

3. A pharmaceutical composition comprising a crystalline form of the compound:

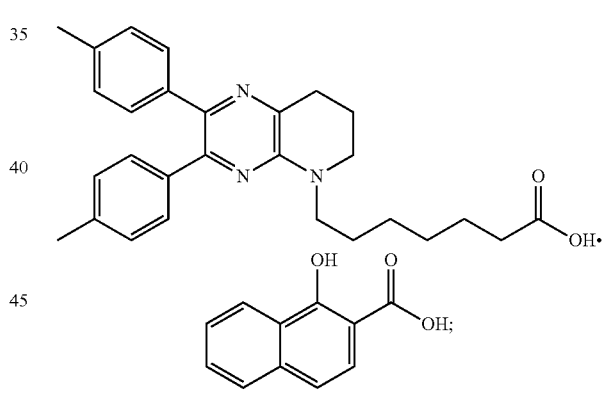

and a pharmaceutically acceptable carrier.

4. A pharmaceutical composition comprising a crystalline form of the compound:

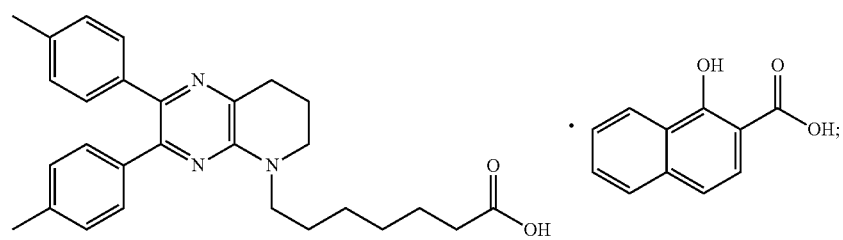 [SMILES: Cc1ccc(-c2nc3c(nc2-c2ccc(C)cc2)N(CCCCCCC(=O)O)CCC3)cc1 ; O=C(O)c1ccc2ccccc2c1O]

and a pharmaceutically acceptable carrier, which is in an inhalable dry powder form.

5. A method of activating prostacyclin receptor in a patient, comprising administering to said patient a therapeutically effective amount of a crystalline form of the compound:

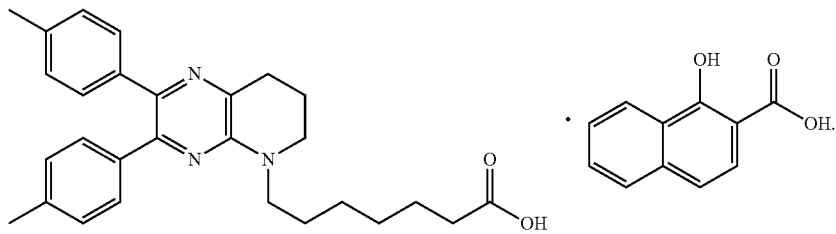 [SMILES: Cc1ccc(-c2nc3c(nc2-c2ccc(C)cc2)N(CCCCCCC(=O)O)CCC3)cc1 ; O=C(O)c1ccc2ccccc2c1O]

6. The method according to claim 5, wherein said patient has pulmonary arterial hypertension.

7. A crystalline form of the compound:

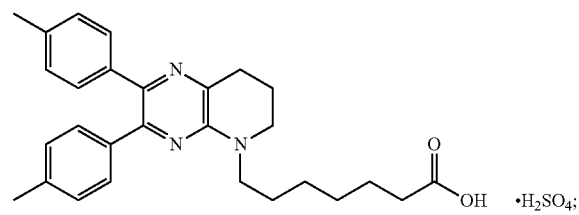

which has the following characteristic diffraction lines (2θ) in the X-ray diffraction pattern thereof: 6.8 °, 9.4° and 22.1 °.

8. A crystalline form of the compound:

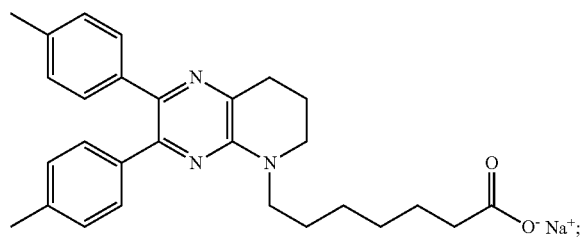

which has the following characteristic diffraction lines (2θ) in the X-ray diffraction pattern thereof: 9.3 °, 18.6° and 22.1°.

9. A crystalline form of the compound:

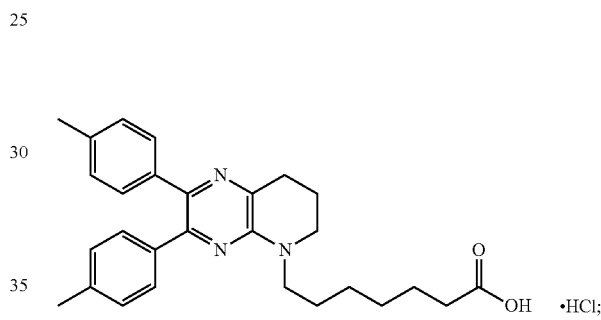

which has the following characteristic diffraction lines (2θ) in the X-ray diffraction pattern thereof: 18.8°, 19.1°, 23.1° and 23.5°.

* * * * *